(12) United States Patent
Cannon et al.

(10) Patent No.: US 10,604,771 B2
(45) Date of Patent: Mar. 31, 2020

(54) DELIVERY METHODS AND COMPOSITIONS FOR NUCLEASE-MEDIATED GENOME ENGINEERING

(71) Applicants: Sangamo BioSciences, Inc., Richmond, CA (US); University of Southern California, Los Angeles, CA (US)

(72) Inventors: Paula M. Cannon, Los Angeles, CA (US); Colin Michael Exline, Los Angeles, CA (US); Michael C. Holmes, Richmond, CA (US)

(73) Assignees: Sangamo Therapeutics, Inc., Richmond, CA (US); University of Southern California, Los Angeles, CA (US)

( * ) Notice: Subject to any disclaimer, the term of this patent is extended or adjusted under 35 U.S.C. 154(b) by 46 days.

(21) Appl. No.: 14/271,008

(22) Filed: May 6, 2014

(65) Prior Publication Data

US 2014/0335063 A1 Nov. 13, 2014

Related U.S. Application Data

(60) Provisional application No. 61/821,872, filed on May 10, 2013.

(51) Int. Cl.
| | |
|---|---|
| *C12N 5/00* | (2006.01) |
| *A61K 48/00* | (2006.01) |
| *C12N 15/90* | (2006.01) |
| *A61K 35/28* | (2015.01) |

(52) U.S. Cl.
CPC ........ *C12N 15/907* (2013.01); *A01K 2207/12* (2013.01); *A01K 2207/15* (2013.01); *A01K 2267/0381* (2013.01); *A61K 35/28* (2013.01)

(58) Field of Classification Search
USPC .............................. 435/455, 325; 424/93.21
See application file for complete search history.

(56) References Cited

U.S. PATENT DOCUMENTS

| | | | |
|---|---|---|---|
| 5,789,538 A | 8/1998 | Rebar et al. | |
| 5,925,523 A | 7/1999 | Dove et al. | |
| 6,007,988 A | 12/1999 | Choo et al. | |
| 6,013,453 A | 1/2000 | Choo et al. | |
| 6,140,081 A | 10/2000 | Barbas, III | |
| 6,140,466 A | 10/2000 | Barbas, III et al. | |
| 6,200,759 B1 | 3/2001 | Dove et al. | |
| 6,242,568 B1 | 6/2001 | Barbas, III et al. | |
| 6,410,248 B1 | 6/2002 | Greisman et al. | |
| 6,453,242 B1 | 9/2002 | Eisenberg et al. | |
| 6,479,626 B1 | 11/2002 | Kim et al. | |
| 6,503,717 B2 | 1/2003 | Case et al. | |
| 6,534,261 B1 | 3/2003 | Cox et al. | |
| 6,599,692 B1 | 6/2003 | Case et al. | |
| 6,607,882 B1 | 8/2003 | Cox et al. | |
| 6,689,558 B2 | 2/2004 | Case | |
| 6,733,970 B2 | 5/2004 | Choo et al. | |
| 6,746,838 B1 | 6/2004 | Choo et al. | |
| 6,794,136 B1 | 9/2004 | Eisenberg et al. | |
| 6,824,978 B1 | 11/2004 | Cox et al. | |
| 6,866,997 B1 | 3/2005 | Choo et al. | |
| 6,903,185 B2 | 6/2005 | Kim et al. | |
| 6,933,113 B2 | 8/2005 | Case et al. | |
| 6,979,539 B2 | 12/2005 | Cox et al. | |
| 7,013,219 B2 | 3/2006 | Case et al. | |
| 7,029,847 B2 | 4/2006 | Joung et al. | |
| 7,030,215 B2 | 4/2006 | Liu et al. | |
| 7,067,317 B2 | 6/2006 | Rebar et al. | |
| 7,070,934 B2 | 7/2006 | Cox, III et al. | |
| 7,153,949 B2 | 12/2006 | Kim et al. | |
| 7,163,824 B2 | 1/2007 | Cox et al. | |
| 7,241,573 B2 | 7/2007 | Choo et al. | |
| 7,241,574 B2 | 7/2007 | Choo et al. | |
| 7,253,273 B2 | 8/2007 | Collingwood | |
| 7,262,054 B2 | 8/2007 | Jamieson et al. | |
| 7,297,491 B2 | 11/2007 | Joung et al. | |
| 7,361,635 B2 | 4/2008 | Miller et al. | |
| 7,364,894 B2* | 4/2008 | Soubrier | C07K 14/501 435/252.3 |
| 7,700,523 B2 | 4/2010 | Choo et al. | |
| 7,914,796 B2 | 3/2011 | Miller et al. | |
| 7,888,121 B2 | 5/2011 | Urnov et al. | |
| 7,951,925 B2* | 5/2011 | Ando | C07K 14/4703 530/300 |
| 7,972,854 B2 | 7/2011 | Miller et al. | |
| 8,034,598 B2 | 10/2011 | Miller et al. | |
| 8,110,379 B2* | 2/2012 | DeKelver | C12N 15/1082 435/455 |
| 8,329,986 B2 | 12/2012 | Butler et al. | |
| 8,409,861 B2 | 4/2013 | Gushin et al. | |
| 8,524,221 B2 | 9/2013 | Ando et al. | |
| 8,586,526 B2 | 11/2013 | Gregory et al. | |
| 8,618,024 B2 | 12/2013 | Choo et al. | |
| 8,623,618 B2 | 1/2014 | Doyon et al. | |
| 2003/0232410 A1 | 12/2003 | Liljedahl et al. | |
| 2005/0026157 A1 | 2/2005 | Baltimore et al. | |
| 2005/0064474 A1* | 3/2005 | Urnov et al. | 435/6 |
| 2005/0208489 A1* | 9/2005 | Carroll et al. | 435/6 |
| 2006/0063231 A1 | 3/2006 | Li et al. | |
| 2007/0134796 A1 | 6/2007 | Holmes et al. | |
| 2008/0131962 A1 | 6/2008 | Miller | |
| 2008/0159996 A1* | 7/2008 | Ando | C07K 14/4703 424/93.21 |
| 2008/0188000 A1* | 8/2008 | Reik et al. | 435/463 |

(Continued)

FOREIGN PATENT DOCUMENTS

| | | |
|---|---|---|
| GB | 2338237 A | 12/1999 |
| WO | WO 98/37186 A1 | 8/1998 |

(Continued)

OTHER PUBLICATIONS

Porteus (Nature Biotech., 2005, vol. 23, No. 8, p. 967-973).*

(Continued)

*Primary Examiner* — Michael C Wilson
(74) *Attorney, Agent, or Firm* — Pasternak Patent Law

(57) ABSTRACT

Disclosed herein are methods and compositions for delivery of engineered nucleases and donor molecules into the genome of a cell.

2 Claims, 8 Drawing Sheets

Specification includes a Sequence Listing.

(56) References Cited

U.S. PATENT DOCUMENTS

| | | | |
|---|---|---|---|
| 2009/0068164 | A1 | 3/2009 | Segal et al. |
| 2009/0305346 | A1 | 12/2009 | Miller |
| 2010/0047805 | A1 | 2/2010 | Wang |
| 2010/0218264 | A1 | 8/2010 | Cui et al. |
| 2010/0291048 | A1 | 11/2010 | Holmes et al. |
| 2011/0160284 | A1 | 6/2011 | Zechiedrich et al. |
| 2011/0201055 | A1 | 8/2011 | Doyon et al. |
| 2011/0207221 | A1 | 8/2011 | Cost et al. |
| 2011/0265198 | A1 | 10/2011 | Gregory et al. |
| 2011/0287545 | A1 | 11/2011 | Cost et al. |
| 2012/0017290 | A1 | 1/2012 | Cui et al. |
| 2012/0042409 | A1 | 2/2012 | Conner et al. |
| 2013/0117870 | A1* | 5/2013 | Fahrenkrug et al. ............ 800/14 |
| 2013/0122591 | A1 | 5/2013 | Cost et al. |
| 2013/0137104 | A1 | 5/2013 | Cost et al. |
| 2013/0177960 | A1* | 7/2013 | Rebar ........................... 435/188 |
| 2013/0177983 | A1* | 7/2013 | Rebar ........................... 435/375 |
| 2013/0209426 | A1* | 8/2013 | Bradley et al. ............ 424/93.21 |

FOREIGN PATENT DOCUMENTS

| | | | |
|---|---|---|---|
| WO | WO 98/53057 | A1 | 11/1998 |
| WO | WO 00/27878 | A1 | 5/2000 |
| WO | WO 01/88197 | A2 | 11/2001 |
| WO | WO 02/077227 | A2 | 10/2002 |
| WO | WO 02/099084 | A2 | 12/2002 |
| WO | WO 07/014275 | A2 | 2/2007 |
| WO | WO 03/016496 | A2 | 2/2008 |
| WO | WO 09/042163 | A2 | 4/2009 |
| WO | WO 10/065123 | A2 | 6/2010 |
| WO | WO 10/079430 | A1 | 7/2010 |
| WO | WO 2010/117464 | * | 10/2010 |
| WO | WO 2011/011767 | * | 1/2011 |
| WO | WO 2011/097036 | * | 8/2011 |
| WO | WO 2011/104382 | * | 9/2011 |
| WO | WO 2012/015938 | * | 2/2012 |
| WO | WO 2013/044008 | * | 3/2013 |
| WO | 2013176772 | A1 | 11/2013 |
| WO | 2013181440 | A1 | 12/2013 |

OTHER PUBLICATIONS

Ramirez (Unexpected failure rates for modular assembly of engineered zinc fingers. Nature Methods, 2008, 5(5): 374-375).*

Geurts (Science, Jul. 24, 2009, vol. 325, p. 433, plus supplemental matieral).*

Christian (Genetics, available online Jul. 26, 2008, vol. 186, p. 757-761).*

Li (Nature, Jul. 14, 2011, vol. 475, No. 7355, p. 217-221, plus Supplemental Material).*

High (Nature, 2005, vol. 435, p. 577 and 579).*

Cui (Clin Exp Metastasis, 2009, vol. 26, p. 849-934, abstract only on p. 883).*

Lombardo (Molecular Therapy, May 2009, vol. 17, No. Suppl. 1, p. S168).*

Papapetrou (Blood, 2010, vol. 116, Abstract 564).*

Benabdallah (Cytotherapy, 2010, 12, 394-399).*

DeKelver (Genome Res., 2010, 1133-1142).*

Hockemeyer (Nature Biotechnol., Jul. 7, 2011, vol. 29, p. 731-734).*

Wang (Circ. Res. Dec. 7, 2012, vol. 111, No. 12, p. 1494-1503).*

Anguela (Blood, Nov. 15, 2013, vol. 122, No. 21, p. 720, 3 page abstract only).*

Deonarain (1998, Expert Opin. Ther. Pat., vol. 8, pp. 53-69).*

Palu (J. Biotechnol., 1999, vol. 68, p. 1-13).*

Luo (Nature Biotechnol., 2000, vol. 18, p. 33-37).*

Pfeifer (Annu. Rev. Genomics. Hum. Genet. 2001, vol. 2, p. 177-211.*

Johnson-Saliba (Curr. Drug. Targets, 2001, vol. 2, p. 371-399).*

Shoji (Current Pharmaceutical Design, 2004, vol. 10, p. 785-796).*

Edelstein (Journal Gene Med., 2004, vol. 6, p. 597-602).*

Moehle (PNAS, 2007, vol. 104, No. 9, p. 3055-3060).*

Lombardo (Nature Biotech., 2007, vol. 25, No. 11, p. 1298-1306).*

Zou (Cell Stem Cell, 2009, vol. 5, No. 1, p. 97-110, plus supplemental).*

Hockemeyer (Nature Biotech., 2009, vol. 27, No. 9, p. 851-857).*

Soldner (Cell, 2010, vol. 146, p. 318-331).*

Darquet (Gene Therapy, 1999, vol. 6, p. 209-218).*

Sharma (Mol. Therapy-Nucleic Acid, published Feb. 26, 2013, vol. 2, e74, p. 1-10).*

Mayrhofer (J. Gene Med., 2008, vol. 10, p. 1253-1269).*

Kay (Nature Biotech., Dec. 2010, vol. 28, No. 12, p. 1287-1289, plus supplemental materials).*

Chen (Human Gene Therapy, 2005, vol. 16, p. 126-131).*

Crystal (Science, 1995, vol. 270, No. 5235, p. 404-410).*

Jia (Nature Methods, 2010, vol. 7, p. 197-199).*

Zou (Cell Stem Cell, 2009, vol. 5, No. 1, p. 97-110).*

Kay (Nature Reviews, 2011, vol. 12, p. 316-328).*

Tasic (PNAS, May 10, 2011, vol. 108, No. 19, p. 7902-7908).*

Perez (Nat Biotechnol. 2008; 26:808-816).*

Chen (Mol. Therapy, Sep. 2003, vol. 8, No. 3, p. 495-500).*

Hou (Mol. Therapy, 2015, vol. No. 14062, p. 1-6).*

Hockemeyer 2011 Supplemental Material.*

Watt (Cytotherapy, 2011, vol. 13, p. 1164-1171).*

Beerli, et al., "Engineering Polydactyl Zinc-Finger Transcription Factors," Nature Biotechnol. 20:135-141 (2002).

Beurdeley, et al., "Compact Designer Talens for Efficient Genome Engineering," Nature Communications 4:1762 (2013) doi:10.10.38/ncomms2782.

Boch, et al., "Breaking The Code of DNA Binding Specificity of Tal-Type III Effectors," Science 326:1509-1512 (2009).

Boissel, et al., "Megatals: A Rare-Cleaving Nuclease Architecture for Therapeutic Genome Engineering," Nucl. Acid Res. 42(4):2591-2601 (2014), doi:10.1093/nar/gkt1224.

Bonas, et al., "Genetic and Structural Characterization of The Avirulence Gene AVRBS3 From Xanthomonas Campestris PV. Vesicatoria," Mol. Gen. Genet. 218:127-136 (1989).

Choo, et al., "Advances in Zinc Finger Engineering," Curr. Opin. Struct. Biol. 10:411-416 (2000).

Christian, et al., "Tal Effector Nucleases Create Targeted DNA Double-Strand Breaks," Genetics epub 10.1534/genetics.110.120717 (2010).

Cong, et al., "Multiplex Genome Engineering Using CRISPR/CAS Systems," Sciencexpress 1/10.1126/science 1231143 (2013).

Darquet, et al., "Minicircle: An Improved DNA Molecule for In Vitro and In Vivo Gene Transfer," Gene Therapy 6:209-218 (1999).

Guo, et al., "Directed Evolution of an Enhanced and Highly Efficient FOKI Cleavage Domain for Zinc Finger Nucleases," J. Mol. Biol. 400(1):96-107 (2010).

Haft, et al., "A Guild of 45 CRISPR-Associated (CAS) Protein Families and Multiple CRISPR/CAS Subtypes Exist in Prokaryotic Genomes," PLoS Comput. Biol. 1:e60 (2005).

Heuer, et al., "Repeat Domain Diversity of AVRBS3-Like Genes in Ralstonia Solanacearum Strains and Association With Host Preferences in the Field," Appl. and Envir. Micro. 73:4379-4384 (2007).

Holt, et al., "Zinc Finger Nuclease-Mediated CCR5 Knockout Hematopoietic Stem Cell Transplantation Controls HIV-1 In Vivo," Nat. Biotechnol. 28(8):839-847 (2010), doi:10.1038/nbt.1663.

Isalan, et al., "A Rapid, Generally Applicable Method to Engineer Zinc Fingers Illustrated by Targeting the HIV-1 Promoter," Nature Biotechnology 19(7):656-660 (2001).

Jansen, et al., "Identification of Genes That Are Associated With DNA Repeats in Prokaryotes," Molecular Microbiology 43(6):1565-1575 (2002).

Kay, et al., "A Bacterial Effector Acts As a Plant Transcription Factor and Induces a Cell Size Regulator," Science 318:648-651 (2007).

Kim, et al., "Hybrid Restriction Enzymes: Zinc Finger Fusions to FOK I Cleavage Domain," PNAS USA 93(3):1156-1160 (1996).

Lombardo, et al., "Gene Editing in Human Stem Cells Using Zinc Finger Nucleases and Integrase-Defective Lentiviral Vector Delivery," Nat. Biotech. 25(11):1298-1306 (2007).

(56) References Cited

OTHER PUBLICATIONS

Makarova, et al., "A DNA Repair System Specific for Thermophilic Archaea and Bacteria Predicted by Genomic Context Analysis," *Nucleic Acids Res.* 30:482-496 (2002).

Makarova, et al., "A Putative RNA-Interference-Based Immune System in Prokaryotes: Computational Analysis of The Predicted Enzymatic Machinery, Functional Analogies With Eukaryotic RNAI, and Hypothetical Mechanisms of Action," *Biol. Direct* 1:7 (2006).

Mayrhofer, et al., "Minicircle-DNA Production by Site Specific Recombination and Protein-DNA Interaction Chromatography," *J. Gene Med.* 10(11):1253-1269 (2008), doi:10.1002/jgm.1243.

Moscou, et al., "A Simple Cipher Governs DNA Recognition by Tal Effectors," *Science* 326:1501 (2009).

Pabo, et al., "Design and Selection of Novel CYS2HIS2 Zinc Finger Proteins," *Ann. Rev. Biochem.* 70:313-340 (2001).

Schornack, et al., "Gene-For-Gene-Mediated Recognition of Nuclear-Targeted AVRBS3-Like Bacterial Effector Proteins," *J. Plant Physiol.* 163:256-272 (2006).

Segal, et al., "Custom DNA-Binding Proteins Come of Age: Polydactyl Zinc-Finger Proteins," *Curr. Opin. Biotechnol.* 12(6):632-637 (2001).

Sharma, et al., "Efficient Sleeping Beauty DNA Transposition From DNA Minicircles," *Molecular Therapy—Nuclear Acids* 2:e74 (2013).

Tebas, et al., "Gene Editing of CCR5 in Autologous CD4 T Cells of Persons Infected With HIV," *New Engl. J. Med.* 370(10):901-910 (2014).

Urnov, et al., "Genome Editing With Engineered Zinc Finger Nucleases," Nature Reviews Genetics 11:636-646 (2010).

Kreiss, et al. "Production of a new DNA vehicle for gene transfer using site-specific recombination," Appl. Micorbiol. 19:650-567 (1998).

Johnson, et al., "Plasmid RK2 ParB Protein: Purification and Nuclease Properties," J. Bacteriol. 181(19): 6010-6018 (1999).

\* cited by examiner

SEQUENCE LISTING

```
<160> NUMBER OF SEQ ID NOS: 3

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gaggattggg aagacaatag cag                                             23

<210> SEQ ID NO 2
<211> LENGTH: 29
<212> TYPE: DNA
<213> ORGANISM: Artificial Sequence
```

-continued

```
<220> FEATURE:
<223> OTHER INFORMATION: Description of Artificial Sequence: Synthetic
      primer

<400> SEQUENCE: 2
ccagcaatag atgatccaac tcaaattcc                                           29

<210> SEQ ID NO 3
<211> LENGTH: 9
<212> TYPE: PRT
<213> ORGANISM: Unknown
<220> FEATURE:
<223> OTHER INFORMATION: Description of Unknown: "LAGLIDADG" family
      peptide motif

<400> SEQUENCE: 3

Leu Ala Gly Leu Ile Asp Ala Asp Gly
1               5
```

US 10,604,771 B2

DELIVERY METHODS AND COMPOSITIONS FOR NUCLEASE-MEDIATED GENOME ENGINEERING

CROSS-REFERENCE TO RELATED APPLICATIONS

The present application claims the benefit of U.S. Provisional Application No. 61/821,872, filed May 10, 2013, the disclosure of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on May 30, 2014, is named 83250107SL.txt and is 1,022 bytes in size.

TECHNICAL FIELD

The present disclosure is in the field of genome engineering, particularly targeted modification of the genome of a cell.

BACKGROUND

Various methods and compositions for targeted cleavage of genomic DNA have been described. Such targeted cleavage events can be used, for example, to induce targeted mutagenesis, induce targeted deletions of cellular DNA sequences, and facilitate targeted recombination at a predetermined chromosomal locus. See, for example, U.S. Pat. Nos. 7,888,121; 7,972,854; 7,914,796; 7,951,925; 8,110,379; 8,409,861; 8,586,526; U.S. Patent Publications 20030232410; 20050208489; 20050026157; 20050064474; 20060063231; 201000218264; 20120017290; 20110265198; 20130137104; 20130122591; 20130177983, 20130177960 and 20150056705, the disclosures of which are incorporated by reference in their entireties for all purposes. These methods often involve the use of engineered cleavage systems to induce a double strand break (DSB) or a nick in a target DNA sequence such that repair of the break by an error prone process such as non-homologous end joining (NHEJ) or repair using a repair template (homology directed repair or HDR) can result in the knock out of a gene or the insertion of a sequence of interest (targeted integration). Cleavage can occur through the use of specific nucleases such as engineered zinc finger nucleases (ZFN), transcription-activator like effector nucleases (TALENs), or using the CRISPR/Cas system with an engineered crRNA/tracr RNA ('single guide RNA') to guide specific cleavage. Clinical trials using cells modified using engineered nucleases have demonstrated therapeutic utility (see, e.g. Tebas et al (2014) *New Eng J Med* 370(10):901).

Targeted cleavage using one of the above mentioned nuclease systems can be exploited to insert a nucleic acid into a specific target location using either HDR or NHEJ-mediated processes. However, delivering both the nuclease system and the donor to the cell can be problematic. For example, delivery of a donor or a nuclease via transduction of a plasmid into the cell can be toxic to the recipient cell, especially to a cell which is a primary cell and so not as robust as a cell from a cell line. Plasmid DNA contains several elements required for its production in bacteria, and is subject to modifications that mark the plasmid as foreign to mammalian cells. Therefore, transfection or nucleofection of plasmid DNA into human cells can cause toxicity. Indeed, genome engineering and transgenic insertion is often an inefficient process due at least in part to the toxicity of the DNA constructs.

DNA minicircles (MCs) are supercoiled DNA molecules that can be used for non-viral gene transfer that have neither an origin of replication or a antibiotic selection marker. These DNAs are devoid of bacterial DNA, and thus lack the unmethylated CpG motifs found in bacterial DNA. These CpG motifs have been shown to active the innate immune response in mammals by binding to the Toll-like receptor 9 receptors on antigen presenting cells. Thus, use of DNAs for gene therapy that contain bacterially derived DNA sequence may be more inflammatory that those DNAs lacking bacterial sequences. MCs are smaller than standard plasmids used in some gene therapy applications, and are more efficiently transfected into both cell lines than standard plasmids (Darquet et al (1999) *Gene Therapy* 6:209-218) and T cells (Sharma et al (2013) *Molecular Therapy-Nucleic Acids* 2 e74). Additionally, DNA MCs are useful for plant cell transformation by either direct DNA uptake by a plant cell, or by use of standard techniques such as *Agrobacterium* mediated transformation or passive uptake; the use of electroporation; treatments with polyethylene glycol; electrophoresis; cell fusion with liposomes or spheroplasts; microinjection; silicon carbide whiskers, and particle bombardment (U.S. Patent publication 20120042409). The MCs can be made through the exploitation of phage integrase φC31-mediated site specific recombination between the attB and attF sites (see Darquet, ibid) and can be produced at large scale.

Thus, there remains a need for compositions and methods for delivery of nucleic acids needed for nuclease-mediated genome engineering to cells that are less toxic and more efficient than currently available methods.

SUMMARY

The present invention describes compositions and methods for use in gene therapy and genome engineering. Specifically, the methods and compositions described relate to DNA minicircle compositions and the use of DNA minicircles ("MCs") for delivery of nucleic acids (e.g., therapeutic nucleic acids) to a cell. Cells that are modified by these DNA MCs are also provided. The DNA MCs described herein may comprise one or more exogenous sequences (e.g., transgenes) and/or one or more nuclease-encoding sequences. Optionally, regions of homology flank the exogenous sequence(s) and/or nuclease-encoding sequences. The nucleic acids delivered by the DNA MCs may comprise nuclease systems for site specific cleavage of a target DNA in the host cell. Also envisioned by the invention are donor (exogenous) nucleic acids that may be delivered to a target cell using the DNA MC and cells comprising sequences integrated into the genome using these DNA MC donors.

In some aspects, the invention comprises delivery of a nuclease to a target cell to result in cleavage at a target locus. In some embodiments, the invention comprises delivery of a nucleic acid encoding one or more nucleases (e.g., a zinc finger nuclease (ZFN), a transcription activator like effector nuclease (TALEN) and/or a CRISPR/Cas system) using a DNA MC. Upon contacting a suitable target cell, the DNA MC is taken up by the cell and the target DNA is cleaved by the expressed nuclease.

In other aspects, the invention comprises a donor nucleic acid for delivery to a target cell. The donor nucleic acid comprises an exogenous sequence (transgene) to be integrated into the genome of the cell, for example, an endogenous locus. In certain aspects, the donor is carried on a minicircle DNA (DNA MC), namely a circular expression cassette lacking most or all (e.g., devoid) of any bacterial plasmid DNA backbone. In some embodiments, the donor comprises a full length gene flanked by regions of homology (homology arms) with the targeted cleavage site. In some embodiments, the donor lacks homologous regions and is integrated into a target locus through homology independent mechanism (i.e. NHEJ). In other embodiments, the donor comprises an smaller piece of nucleic acid flanked by homologous regions for use in the cell (i.e. for gene correction). In some embodiments, the donor comprises a gene encoding a functional or structural component such as a shRNA, RNAi, miRNA or the like. Cells including the transgene integrated into a target site using a nuclease are also provided.

The sequence of interest of the donor molecule may comprise one or more sequences encoding a functional polypeptide (e.g., a cDNA), with or without a promoter. In certain embodiments, the nucleic acid sequence comprises a sequence encoding an antibody, an antigen, an enzyme, a growth factor, a receptor (cell surface or nuclear), a hormone, a lymphokine, a cytokine, a reporter, functional fragments of any of the above and combinations of the above. In embodiments in which the functional polypeptide encoding sequences are promoterless, expression of the integrated sequence is then ensured by transcription driven by an endogenous promoter or other control element in the region of interest. In other embodiments, a "tandem" cassette is integrated into the selected site in this manner, the first component of the cassette comprising a promoterless sequence as described above, followed by a transcription termination sequence, and a second sequence, encoding an autonomous expression cassette. Additional sequences (coding or non-coding sequences) may be included in the donor molecule between the homology arms, including but not limited to, sequences encoding a 2A peptide, SA site, IRES, etc.

In another aspect, described herein are methods of integrating a donor nucleic acid into the genome of a cell via homology-independent mechanisms. The methods comprise creating a double-stranded break (DSB) in the genome of a cell and cleaving the donor molecule using a nuclease, such that the donor nucleic acid is integrated at the site of the DSB. In certain embodiments, the donor nucleic acid is integrated via non-homology dependent methods (e.g., NHEJ). As noted above, upon in vivo cleavage the donor sequences can be integrated in a targeted manner into the genome of a cell at the location of a DSB. The donor sequence can include one or more of the same target sites for one or more of the nucleases used to create the DSB. Thus, the donor sequence may be cleaved by one or more of the same nucleases used to cleave the endogenous gene into which integration is desired. In certain embodiments, the donor sequence includes different nuclease target sites from the nucleases used to induce the DSB. DSBs in the genome of the target cell may be created by any mechanism. In certain embodiments, the DSB is created by one or more zinc-finger nucleases (ZFNs), fusion proteins comprising a zinc finger binding domain, which is engineered to bind a sequence within the region of interest, and a cleavage domain or a cleavage half-domain. In other embodiments, the DSB is created by one or more TALE DNA-binding domains (naturally occurring or non-naturally occurring) fused to a nuclease domain (TALEN). In yet further embodiments, the DSB is created using a CRISPR/Cas nuclease system where an engineered single guide RNA or its functional equivalent is used to guide the nuclease to a targeted site in a genome. In some embodiments, the nuclease(s) and/or the donors are delivered to the cell using a DNA MC.

In other aspects, the nuclease(s) binds to and/or cleaves a safe-harbor gene, for example a CCR5 gene, an HPRT gene, a PPP1R12C (also known as AAVS1) gene, or a Rosa gene in mammalian cells, and the Zp15 locus in plants. See, e.g., U.S. Pat. Nos. 7,951,925; 8,110,379 and 8,329,986; U.S. Publication Nos. 20080159996; 201000218264; 20100291048; 20120017290; 20110265198; 20130137104; 20130122591; 20130177983, 20130177960 and 20150056705. In some embodiments, the nuclease(s) bind to and/or target a site for directing the expression of a transgene (e.g. albumin). See, e.g. U.S. Publication Nos. 20130177983 and 20130177960.

In one aspect, the DNA MCs are used to deliver regulatory proteins of interest (e.g. ZFP TFs, TALE TFs or a CRISPR/Cas TF) to bind to and/or modulate expression of a gene of interest. In one embodiment, the regulatory proteins bind to a DNA sequence and prevent binding of other regulatory factors. In another embodiment, the binding of the regulatory protein may modulate (i.e. induce or repress) expression of a target DNA.

In another aspect, described herein is a method for reducing toxic effects (toxicity) in a cell modified via nuclease-mediated integration of an exogenous sequence (donor), the method comprising administering nuclease-encoding sequences and/or exogenous sequence (donor or transgene) using DNA MCs, whereby toxicity in the cell is reduced as compared to a cell in which the exogenous sequence is introduced using a plasmid vector or a viral vector. In some embodiments, the donor sequences are carried on DNA MCs and the nuclease(s) is(are) delivered in mRNA form. In other embodiments, the donor sequences are carried on DNA MCs and the nucleases are carried on plasmids or viral vectors (e.g., adenovirus, AAV, etc.) In still further embodiments, both the nuclease(s) and the donor are carried on DNA MCs.

In yet another aspect, described herein is a cell or cell line comprising a DNA MC as described herein or a descendent of such a cell that includes a genetic modification made using one or more DNA MCs as described herein.

In any of the methods and compositions (e.g., cells) described herein, the cell can be any eukaryotic cells, for example a plant cell or a mammalian cell or cell line, including COS, CHO (e.g., CHO-S, CHO-K1, CHO-DG44, CHO-DUXB11, CHO-DUKX, CHOK1SV), VERO, MDCK, WI38, V79, B14AF28-G3, BHK, HaK, NS0, SP2/0-Ag14, HeLa, HEK293 (e.g., HEK293-F, HEK293-H, HEK293-T), and perC6 cells as well as insect cells such as *Spodoptera fugiperda* (Sf), or fungal cells such as *Saccharomyces, Pichia* and *Schizosaccharomyces*. In certain embodiments, the cell line is a CHO, MDCK or HEK293 cell line. Suitable cells also include stem cells such as, by way of example, embryonic stem cells, induced pluripotent stem cells, hematopoietic stem cells (e.g., CD34+), neuronal stem cells and mesenchymal stem cells.

In other aspects, methods of using the cells as described herein for the generation of animal models and/or treatment or prevention of a condition are described. In certain embodiments, genetically modified blood cell precursors (hematopoietic stem cells known as "HSCs") are given in a bone marrow transplant and the HSCs differentiate and mature in vivo in a subject (e.g., animal model or human). In some embodiments, the HSCs are isolated following G-CSF-induced mobilization, and in others, the cells are isolated from human bone marrow or umbilical cords. In some aspects, the HSCs are edited by treatment with a nuclease designed to knock out a specific gene or regulatory sequence. In other aspects, the HSCs are modified with an engineered nuclease and a donor nucleic acid such that a wild type gene or other gene of interest is inserted and expressed and/or an endogenous aberrant gene is corrected. In some embodiments, the modified HSCs are administered to the subject (patient) following mild myeloablative preconditioning. In other aspects, the HSCs are administered after full myeloablation such that following engraftment, 100% of the hematopoietic cells are derived from the modified HSCs. Furthermore, the cell may be arrested in the G2 phase of the cell cycle.

In some embodiments of the methods and compositions described herein, the cell may be one lacking efficient homology-based DNA repair, for example a CHO cell. In certain embodiments, the cells may be primary or non-dividing cells which preferentially use the NHEJ DNA repair pathway.

In some embodiments, the methods and compositions of the invention comprise plant cells. In some embodiments, the plant cells comprise a nuclease of the invention. In other embodiments, the plant cells additionally comprise a transgene. In some embodiments, the nuclease(s) and/or transgene is introduced into the plant cell via a DNA MC. In yet another aspect, described herein is a method for introducing one or more exogenous sequence into the genome of a plant cell, the method comprising the steps of: (a) contacting the cell with the one or more exogenous sequences (donor vector, transgene or GOI); and (b) expressing one or more nucleases (e.g., ZFN, TALEN or CRISPR/Cas system) as described herein in the cell, wherein the one or more nucleases cleave chromosomal DNA; such that cleavage of chromosomal DNA in step (b) stimulates incorporation of the donor vector into the genome by homologous recombination. Multiple transgenes may be integrated simultaneously (in parallel) or the steps may be repeated for sequential addition of transgenes (transgene stacking).

In any of the compositions (cells or plants) or methods described herein, the plant cell can comprise a monocotyledonous or dicotyledonous plant cell. In certain embodiments, the plant cell is a crop plant, for example, tomato (or other fruit crop), potato, maize, soy, alfalfa, etc.

In a still further aspect, an animal or plant cell obtained according to any of the methods described herein is also provided.

In another aspect, provided herein is a plant comprising a plant cell as described herein. In yet another aspect provided herein is an animal comprising an animal cell as described herein.

In another aspect, provided herein is a seed from a plant comprising the plant cell that is obtained as described herein.

In another aspect, provided herein is fruit obtained from a plant comprising plant cell obtained as described herein.

In some embodiments, the transgenic cell, plant and/or animal includes a transgene that encodes a human gene. In some instances, the transgenic animal comprises a knock out at the endogenous locus corresponding to exogenous transgene, thereby allowing the development of an in vivo system where the human protein may be studied in isolation. Such transgenic models may be used for screening purposes to identify small molecules or large biomolecules or other entities which may interact with or modify the human protein of interest. In some aspects, the transgene is integrated into the selected locus (e.g., safe-harbor) into a stem cell (e.g., an embryonic stem cell, an induced pluripotent stem cell, a hematopoietic stem cell, etc.) or animal embryo obtained by any of the methods described herein, and then the embryo is implanted such that a live animal is born. The animal is then raised to sexual maturity and allowed to produce offspring wherein at least some of the offspring comprise edited endogenous gene sequence or the integrated transgene.

A kit, comprising the DNA MCs of the invention, is also provided. The kit may comprise DNA MCs encoding the nucleases, (e.g. RNA molecules or ZFN, TALEN or CRISPR/Cas system encoding genes contained in a suitable expression vector), or aliquots of the nuclease proteins, donor molecules, suitable host cell lines, instructions for performing the methods of the invention, and the like. The DNA MCs may also comprise donor molecules of interest for use in the kit.

These and other aspects will be readily apparent to the skilled artisan in light of disclosure as a whole.

BRIEF DESCRIPTION OF THE DRAWINGS

FIG. 1A is a schematic showing the plasmid donor designated "P2U," which is 8.2 Kb, to deliver the GFP transgene ("GFP") to a targeted site in the human CCR5 gene. The plasmid has two regions homologous to the human CCR5 gene, and flanking the target site of the CCR5 ZFN pair. The homology region to the right of the GFP is 1.5 Kb, while the homology region to the left of GFP is 0.5 Kb. Expression of the GFP is driven by the UbC promoter and the construct also contains a polyadenylation signal sequence ("pA"). The plasmid backbone sequences which include a bacterial origin of replication and an ampicillin resistance gene are indicated by the solid curved line. FIG. 1B shows the comparator MC donor, M2U, which is about 4.5 Kb. The MC has the same transgene and CCR5 homology arm features as the P2U plasmid, but lacks the bacterial plasmid backbone in the final product. Instead, the MC contains approximately 150 base pairs of residual plasmid sequence of non-bacterial origin (e.g., approximately 36 base pairs of an attR recombination site, and a varying length of sequence referred to as a 'multiple cloning site' that facilitates construction of a specific MC) that remain after construction of M2U, indicated by the dashed line. FIG. 1C shows a linear donor PCR product ("PCR2U") also used for donor delivery that is approximately 4.3 Kb. PCR2U has the same transgene and CCR homology arm features described above for P2U and M2U, but contains no bacterial or residual plasmid sequences. FIG. 1D shows the plasmid donor construct designated "P1P" (6.1 Kb) which is similar to the plasmid donor shown in FIG. 1A, except that the right homology arm has been shortened to approximately 0.5 Kb, and a PGK promoter is used to drive the GFP. FIG. 1E depicts a MC equivalent of P1P designated "M1P," which is 2.6 Kb, where the bacterial backbone sequences have been removed and only a residual region of approximately 150 bp of DNA remains from the process of making the MC, indicated by the dashed line.

FIG. 2A depicts a comparison of the standard plasmid donor P2U versus M1P on toxicity following electroporation. The values shown represent the percent increase in cell death caused by the introduction of the indicated constructs into the HSC compared to the level of cell death occurring in untreated HSC maintained in culture, as assayed by 7-Amino-actinomycin D (7-AAD) exclusion. 7-AAD intercalates into double-stranded nucleic acids and is excluded by viable cells but can penetrate cell membranes of dying or dead cells. Also shown are the number of independent experiments (n=). FIG. 2B depicts a comparison of the plasmid donor P2U with M2U and the linear PCR product donor PCR2U. The values shown indicate the percent increase in cell death compared to untreated HSC.

FIG. 3A shows the resulting human CD45+ cell levels following engraftment of HSC in NSG mice, where the precursor HSC had been treated either with ZFN mRNAs alone, or ZFN mRNA in combination with the standard plasmid donor, P2U, or the MC DNA donor, M1P. Each point represents the human CD45+ cell count in the peripheral blood of an NSG mouse following engraftment, where measurements were taken at 4, 8, 12, 16 and 20 weeks post-engraftment; as well as in bone marrow and spleen of the mice at necroscopy at 20 weeks. FIG. 3B shows a similar data set as for FIG. 3A, but with a separate cohort of mice. FIG. 3C shows the overall engraftment levels of the human CD45+ leucocyte populations resulting from engraftment of mice with HSC that had been nucleofected with ZFN mRNAs in combination either P1P or M1P, as measured in the blood of NSG mice at either 8 or 12 weeks post introduction of the cells. FIG. 3D shows the frequency of the differentiated CD19+ B cells, CD4 T cells and CD8 T cells, respectively, within these human CD45+ cell populations. Only those blood samples that have greater than 5% human CD45+ cells provide enough cells to be reasonably be used in these subset analyses, and none of the P1P blood samples met this threshold as shown in FIG. 3C.

FIG. 4A depicts the comparison of the P2U plasmid with the MC donor M1P, both with and without the co-expression of ZFNs, where the percent of cells expressing GFP was measured by FACS over time post-nucleofection. In the absence of ZFNs, there is only a background level of GFP expression by day 4 in culture, since gene addition is a very rare event. Much higher levels of GFP gene addition occur when the ZFNs are also present, and the MC donor M1P gives, on average, >3-fold higher rates compared to the plasmid donor P2U (graph on the right). FIG. 4B depicts the comparison of P1P with M1P, while

FIGS. 5A and B compare the levels of specific integration achieved by plasmid donor P2U and MC donor M1P. FIG. 5A displays the percent of PCR product detected for each donor while FIG. 5B depicts the relative fold-increase in integration from the DNA MC donor versus the plasmid donor. The results demonstrate that there is a 2.5 fold increase in targeted integration when the donor is delivered via a DNA MC in comparison with standard plasmid donor delivery. FIG. 5C shows the results of the in-out PCR analysis for two independent experiments comparing MC donor M2U to plasmid donor P2U. The darker band of product observed with M2U donor indicates higher levels of specific gene addition at the targeted CCR5 locus.

DETAILED DESCRIPTION

Figure 1:
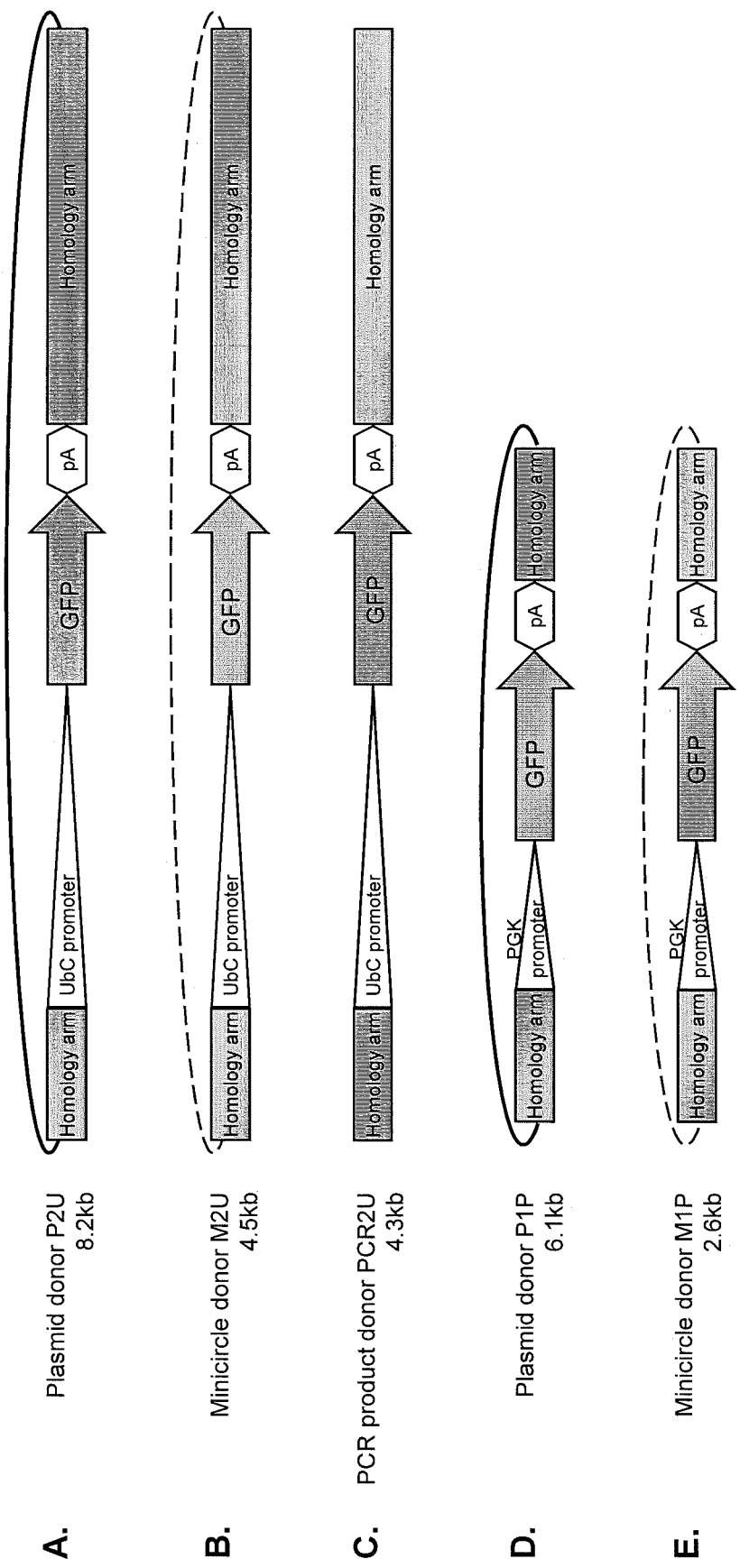
FIG. 1, panels A to E, are schematics of donor constructs (A-E) used. Constructs were made to compare MC donors with standard plasmid donors or PCR products.

Disclosed herein are compositions and methods for nuclease-mediated (e.g., NHEJ or HDR capture) targeted integration of a transgene. In particular, nuclease-mediated (i.e. ZFN, TALEN and/or CRISPR/Cas system) targeted integration of an exogenous sequence is efficiently achieved using a DNA MC. These smaller DNA circles are essentially devoid of bacterial sequences, and thus are less toxic to the target cells. In fact, we demonstrate here that integration is increased by approximately 2.5 fold when donor is delivered via a DNA MC. Furthermore, the reduction in toxicity will likely extend to the delivery of the DNAs encoding the nucleases as well, when both the nucleases and the donors can be delivered to a cell of interest using one or more DNA minicircles.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these teens are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

A "TALE DNA binding domain" or "TALE" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein.

Zinc finger and TALE binding domains can be "engineered" to bind to a predetermined nucleotide sequence, for example via engineering (altering one or more amino acids) of the recognition helix region of a naturally occurring zinc finger or TALE protein. Therefore, engineered DNA binding proteins (zinc fingers or TALEs) are proteins that are non-naturally occurring. Non-limiting examples of methods for engineering DNA-binding proteins are design and selection. A designed DNA binding protein is a protein not occurring in nature whose design/composition results principally from rational criteria. Rational criteria for design include application of substitution rules and computerized algorithms for processing information in a database storing information of existing ZFP and/or TALE designs and binding data. See, for example, U.S. Pat. Nos. 8,586,526; 6,140,081; 6,453,242; 6,746,838; 7,241,573; 6,866,997; 7,241,574 and 6,534,261; see also WO 03/016496.

A "selected" zinc finger protein or TALE is a protein not found in nature whose production results primarily from an empirical process such as phage display, interaction trap or hybrid selection. See e.g., U.S. Pat. Nos. 8,586,526; 5,789,538; 5,925,523; 6,007,988; 6,013,453; 6,200,759; 6,242,568; 6,733,970; 7,297,491; WO 98/53057; WO 02/099084.

"Recombination" refers to a process of exchange of genetic information between two polynucleotides, including but not limited to, donor capture by non-homologous end joining (NHEJ) and homologous recombination. For the purposes of this disclosure, "homologous recombination (HR)" refers to the specialized form of such exchange that takes place, for example, during repair of double-strand breaks in cells via homology-directed repair mechanisms. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

In the methods of the disclosure, one or more targeted nucleases as described herein create a double-stranded break in the target sequence (e.g., cellular chromatin) at a predetermined site, and a "donor" polynucleotide, having homology to the nucleotide sequence in the region of the break, can be introduced into the cell. The presence of the double-stranded break has been shown to facilitate integration of the donor sequence. The donor sequence may be physically integrated or, alternatively, the donor polynucleotide is used as a template for repair of the break via homologous recombination, resulting in the introduction of all or part of the nucleotide sequence as in the donor into the cellular chromatin. Thus, a first sequence in cellular chromatin can be altered and, in certain embodiments, can be converted into a sequence present in a donor polynucleotide. Thus, the use of the terms "replace" or "replacement" can be understood to represent replacement of one nucleotide sequence by another, (i.e., replacement of a sequence in the informational sense), and does not necessarily require physical or chemical replacement of one polynucleotide by another.

In any of the methods described herein, additional nucleases (e.g., zinc-finger nucleases, TALEN and/or CRISPR/Cas) can be used for additional double-stranded cleavage of additional target sites within the cell.

Any of the methods described herein can be used for insertion of a donor of any size and/or partial or complete inactivation of one or more target sequences in a cell by targeted integration of donor sequence that disrupts expression of the gene(s) of interest. Cells and cell lines with partially or completely inactivated genes are also provided.

Furthermore, the methods of targeted integration as described herein can also be used to integrate one or more exogenous sequences. The exogenous nucleic acid sequence can comprise, for example, one or more genes or cDNA molecules, or any type of coding or noncoding sequence, as well as one or more control elements (e.g., promoters). In addition, the exogenous nucleic acid sequence may produce one or more RNA molecules (e.g., small hairpin RNAs (shRNAs), inhibitory RNAs (RNAis), microRNAs (miRNAs), etc.).

In certain embodiments of methods for targeted recombination and/or replacement and/or alteration of a sequence in a region of interest in cellular chromatin, a chromosomal sequence is altered by homologous recombination with an exogenous "donor" nucleotide sequence. Such homologous recombination is stimulated by the presence of a double-stranded break in cellular chromatin, if sequences homologous to the region of the break are present. In other embodiments, targeted alteration is via non-homology dependent mechanisms, for example, non-homologous end joining (NHEJ). See, e.g., U.S. Patent Publication Nos. 20110207221 and 20110287545.

In any of the methods described herein, the exogenous nucleotide sequence (the "donor sequence" or "transgene") can contain sequences that are homologous, but not identical, to genomic sequences in the region of interest, thereby stimulating homologous recombination to insert a non-identical sequence in the region of interest. Thus, in certain embodiments, portions of the donor sequence that are homologous to sequences in the region of interest exhibit between about 80 to 99% (or any integer therebetween) sequence identity to the genomic sequence that is replaced. In other embodiments, the homology between the donor and genomic sequence is higher than 99%, for example if only 1 nucleotide differs as between donor and genomic sequences of over 100 contiguous base pairs. In certain cases, a non-homologous portion of the donor sequence can contain sequences not present in the region of interest, such that new sequences are introduced into the region of interest. In these instances, the non-homologous sequence is generally flanked by sequences of 50-1,000 base pairs (or any integral value therebetween) or any number of base pairs greater than 1,000, that are homologous or identical to sequences in the region of interest. In other embodiments, the donor sequence is non-homologous to the first sequence, and is inserted into the genome by non-homologous recombination mechanisms.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. Pat. Nos. 7,888,121; 7,914,796; 8,034,598; 8,623,618 and U.S. Patent Publication No. 20110201055, incorporated herein by reference in their entireties.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 100,000,000 nucleotides in length (or any integer value therebetween or therabove), preferably between about 10 and 100,000 nucleotides in length (or any integer therebetween), more preferably between about 2000 and 20,000 nucleotides in length (or any value therebetween), more preferable, between about 5 and 15 kb and even more preferably between 0.5 and 2 kb (or any value therebetween). The donor sequence may be single- and/or double-stranded.

A "homologous, non-identical sequence" refers to a first sequence which shares a degree of sequence identity with a second sequence, but whose sequence is not identical to that of the second sequence. For example, a polynucleotide comprising the wild-type sequence of a mutant gene is homologous and non-identical to the sequence of the mutant gene. In certain embodiments, the degree of homology between the two sequences is sufficient to allow homologous recombination therebetween, utilizing normal cellular mechanisms. Two homologous non-identical sequences can be any length and their degree of non-homology can be as small as a single nucleotide (e.g., for correction of a genomic point mutation by targeted homologous recombination) or as large as 10 or more kilobases (e.g., for insertion of a gene at a predetermined ectopic site in a chromosome). Two polynucleotides comprising the homologous non-identical sequences need not be the same length. For example, an exogenous polynucleotide (i.e., donor polynucleotide) of between 20 and 10,000 nucleotides or nucleotide pairs can be used.

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) can be compared by determining their percent identity using standard techniques. Typically the percent identities between sequences are at least 70-75%, preferably 80-82%, more preferably 85-90%, even more preferably 92%, still more preferably 95%, and most preferably 98% sequence identity.

Alternatively, the degree of sequence similarity between polynucleotides can be determined by hybridization of polynucleotides under conditions that allow formation of stable duplexes between homologous regions, followed by digestion with single-stranded-specific nuclease(s), and size determination of the digested fragments. Two nucleic acid, or two polypeptide sequences are substantially homologous to each other when the sequences exhibit at least about 70%-75%, preferably 80%-82%, more preferably 85%-90%, even more preferably 92%, still more preferably 95%, and most preferably 98% sequence identity over a defined length of the molecules, as determined using the methods known in the art. Conditions for hybridization are well-known to those of skill in the art. Hybridization stringency refers to the degree to which hybridization conditions disfavor the formation of hybrids containing mismatched nucleotides, with higher stringency correlated with a lower tolerance for mismatched hybrids. Factors that affect the stringency of hybridization are well-known to those of skill in the art and include, but are not limited to, temperature, pH, ionic strength, and concentration of organic solvents such as, for example, formamide and dimethylsulfoxide. As is known to those of skill in the art, hybridization stringency is increased by higher temperatures, lower ionic strength and lower solvent concentrations.

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

An "accessible region" is a site in cellular chromatin in which a target site present in the nucleic acid can be bound by an exogenous molecule which recognizes the target site. Without wishing to be bound by any particular theory, it is believed that an accessible region is one that is not packaged into a nucleosomal structure. The distinct structure of an accessible region can often be detected by its sensitivity to chemical and enzymatic probes, for example, nucleases.

A "target site" or "target sequence" is a nucleic acid sequence that defines a portion of a nucleic acid to which a binding molecule will bind, provided sufficient conditions for binding exist.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer. An exogeneous molecule can also be the same type of molecule as an endogenous molecule but derived from a different species than the cell is derived from. For example, a human nucleic acid sequence may be introduced into a cell line originally derived from a mouse or hamster. Methods for the introduction of exogenous molecules into plant cells are known to those of skill in the art and include, but are not limited to, protoplast transformation, silicon carbide (e.g., WHISKERS™), *Agrobacterium*-mediated transformation, lipid-mediated transfer (i.e., liposomes, including neutral and cationic lipids), electroporation, direct injection, cell fusion, particle bombardment (e.g., using a "gene gun"), calcium phosphate co-precipitation, DEAE-dextran-mediated transfer and viral vector-mediated transfer.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

As used herein, the term "product of an exogenous nucleic acid" includes both polynucleotide and polypeptide products, for example, transcription products (polynucleotides such as RNA) and translation products (polypeptides).

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP or TALE DNA-binding domain and one or more activation domains) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression. Genome editing (e.g., cleavage, alteration, inactivation, random mutation) can be used to modulate expression. Gene inactivation refers to any reduction in gene expression as compared to a cell that does not include a ZFP, TALE or CRISPR/Cas system as described herein. Thus, gene inactivation may be partial or complete.

"Plant" cells include, but are not limited to, cells of monocotyledonous (monocots) or dicotyledonous (dicots) plants. Non-limiting examples of monocots include cereal, plants such as maize, rice, barley, oats, wheat, sorghum, rye, sugarcane, pineapple, onion, banana, and coconut. Non-limiting examples of dicots include tobacco, tomato, sunflower, cotton, sugarbeet, potato, lettuce, melon, soy, canola (rapeseed), and alfalfa. Plant cells may be from any part of the plant and/or from any stage of plant development.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

"Eukaryotic" cells include, but are not limited to, fungal cells (such as yeast), plant cells and animal cells, including mammalian cells and human cells (e.g., stem cells).

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP, TALE or Cas DNA-binding domain is fused to an activation domain, the ZFP, TALE or Cas DNA-binding domain and the activation domain are in operative linkage if, in the fusion polypeptide, the ZFP, TALE of Cas DNA-binding domain portion is able to bind its target site and/or its binding site, while the activation domain is able to upregulate gene expression. When a fusion polypeptide in which a ZFP, TALE or Cas DNA-binding domain is fused to a cleavage domain, the ZFP, TALE or Cas DNA-binding domain and the cleavage domain are in operative linkage if, in the fusion polypeptide, the ZFP, TALE or Cas DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) Nature 340:245-246; U.S. Pat. No. 5,585,245 and PCT WO 98/44350.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors.

A "reporter gene" or "reporter sequence" refers to any sequence that produces a protein product that is easily measured, preferably although not necessarily in a routine assay. Suitable reporter genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence. "Expression tags" include sequences that encode reporters that may be operably linked to a desired gene sequence in order to monitor expression of the gene of interest.

A "safe harbor" locus is a locus within the genome wherein a gene may be inserted without any deleterious effects on the host cell. Most beneficial is a safe harbor locus in which expression of the inserted gene sequence is not perturbed by any read-through expression from neighboring genes. Non-limiting examples safe harbor loci in mammalian cells include, for example, a CCR5 gene, a CXCR4 gene, a PPP1R12C (also known as AAVS1) gene, an albumin gene or a Rosa gene. See, e.g., U.S. Pat. Nos. 7,951,925 and 8,110,379; U.S. Publication Nos. 201000218264; 20100291048; 20120017290; 20110265198; 20130137104; 20130122591; 20130177983 and 20130177960. An exemplary safe harbor in a plant cell is the ZP15 locus (U.S. Pat. No. 8,329,986).

The terms "subject" and "patient" are used interchangeably and refer to mammals such as human patients and non-human primates, as well as experimental animals such as rabbits, dogs, cats, rats, mice, rabbits and other animals. Accordingly, the term "subject" or "patient" as used herein means any mammalian patient or subject to which the or stem cells of the invention can be administered.

Nucleases

Described herein are compositions, particularly nucleases, that are useful for in vivo cleavage of a donor molecule carrying a transgene and nucleases for cleavage of the genome of a cell such that the transgene is integrated into the genome in a targeted manner. In certain embodiments, one or more of the nucleases are naturally occurring. In other embodiments, one or more of the nucleases are non-naturally occurring, i.e., engineered in the DNA-binding domain and/or cleavage domain. For example, the DNA-binding domain of a naturally-occurring nuclease may be altered to bind to a selected target site (e.g., a meganuclease that has been engineered to bind to site different than the cognate binding site). In other embodiments, the nuclease comprises heterologous DNA-binding and cleavage domains (e.g., zinc finger nucleases; TAL-effector domain DNA binding proteins; meganuclease DNA-binding domains with heterologous cleavage domains).

A. DNA-Binding Domains

In certain embodiments, the composition and methods described herein employ a meganuclease (homing endonuclease) DNA-binding domain for binding to the donor molecule and/or binding to the region of interest in the genome of the cell. Naturally-occurring meganucleases recognize 15-40 base-pair cleavage sites and are commonly grouped into four families: the LAGLIDADG family ("LAGLIDADG" disclosed as SEQ ID NO: 3), the GIY-YIG family, the His-Cyst box family and the HNH family. Exemplary homing endonucleases include I-SceI, I-CeuI, PI-PspI, PI-Sce, I-SceIV, CsmI, I-PanI, I-SceII, I-PpoI, I-SceIII, I-CreI, I-TevI, I-TevII and I-TevIII. Their recognition sequences are known. See also U.S. Pat. Nos. 5,420,032; 6,833,252; Belfort et al. (1997) *Nucleic Acids Res.* 25:3379-3388; Dujon et al. (1989) *Gene* 82:115-118; Perler et al. (1994) Nucleic Acids Res. 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue.

In certain embodiments, the methods and compositions described herein make use of a nuclease that comprises an engineered (non-naturally occurring) homing endonuclease (meganuclease). The recognition sequences of homing endonucleases and meganucleases such as I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII are known. See also U.S. Pat. Nos. 5,420,032; 6,833,252 and 8,021,867; Belfort et al. (1997) *Nucleic Acids Res.* 25:3379-3388; Dujon et al. (1989) *Gene* 82:115-118; Perler et al. (1994) *Nucleic Acids Res.* 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue. In addition, the DNA-binding specificity of homing endonucleases and meganucleases can be engineered to bind non-natural target sites. See, for example, Chevalier et al. (2002) *Molec. Cell* 10:895-905; Epinat et al. (2003) *Nucleic Acids Res.* 31:2952-2962; Ashworth et al. (2006) *Nature* 441:656-659; Paques et al. (2007) *Current Gene Therapy* 7:49-66. The DNA-binding domains of the homing endonucleases and meganucleases may be altered in the context of the nuclease as a whole (i.e., such that the nuclease includes the cognate cleavage domain) or may be fused to a heterologous cleavage domain.

In other embodiments, the DNA-binding domain of one or more of the nucleases used in the methods and compositions described herein comprises a naturally occurring or engineered (non-naturally occurring) TAL effector DNA binding domain. See, e.g., U.S. Pat. No. 8,586,526, incorporated by reference in its entirety herein. The plant pathogenic bacteria of the genus *Xanthomonas* are known to cause many diseases in important crop plants. Pathogenicity of *Xanthomonas* depends on a conserved type III secretion (T3S) system which injects more than 25 different effector proteins into the plant cell. Among these injected proteins are transcription activator-like (TAL) effectors which mimic plant transcriptional activators and manipulate the plant transcriptome (see Kay et al (2007) *Science* 318:648-651). These proteins contain a DNA binding domain and a transcriptional activation domain. One of the most well characterized TAL-effectors is AvrBs3 from *Xanthomonas campestgris* pv. *Vesicatoria* (see Bonas et al (1989) *Mol Gen Genet* 218: 127-136 and WO2010079430). TAL-effectors contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack S, et al (2006) *J Plant Physiol* 163(3): 256-272). In addition, in the phytopathogenic bacteria *Ralstonia solanacearum* two genes, designated brg11 and hpx17 have been found that are homologous to the AvrBs3 family of *Xanthomonas* in the *R. solanacearum* biovar 1 strain GMI1000 and in the biovar 4 strain RS1000 (See Heuer et al (2007) *Appl and Envir Micro* 73(13): 4379-4384). These genes are 98.9% identical in nucleotide sequence to each other but differ by a deletion of 1,575 bp in the repeat domain of hpx17. However, both gene products have less than 40% sequence identity with AvrBs3 family proteins of *Xanthomonas*.

Specificity of these TAL effectors depends on the sequences found in the tandem repeats. The repeated sequence comprises approximately 102 bp and the repeats are typically 91-100% homologous with each other (Bonas et al, ibid). Polymorphism of the repeats is usually located at positions 12 and 13 and there appears to be a one-to-one correspondence between the identity of the hypervariable diresidues at positions 12 and 13 with the identity of the contiguous nucleotides in the TAL-effector's target sequence (see Moscou and Bogdanove, (2009) *Science*

326:1501 and Boch et al (2009) *Science* 326:1509-1512). Experimentally, the natural code for DNA recognition of these TAL-effectors has been determined such that an HD sequence at positions 12 and 13 leads to a binding to cytosine (C), NG binds to T; NI to A; HD binds to C; and NN binds to A or G. These DNA binding repeats have been assembled into proteins with new combinations and numbers of repeats, to make artificial transcription factors that are able to interact with new sequences and activate the expression of a non-endogenous reporter gene in plant cells (Boch et al, ibid). Engineered TAL proteins have been linked to a FokI cleavage half domain to yield a TAL effector domain nuclease fusion (TALEN) exhibiting activity in a yeast reporter assay (plasmid based target). See, e.g., U.S. Pat. No. 8,586,526; Christian et al ((2010)<*Genetics* epub 10.1534/genetics.110.120717).

In certain embodiments, the DNA binding domain of one or more of the nucleases used for in vivo cleavage and/or targeted cleavage of the genome of a cell comprises a zinc finger protein. Preferably, the zinc finger protein is non-naturally occurring in that it is engineered to bind to a target site of choice. See, for example, See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416; U.S. Pat. Nos. 7,888,121; 7,972,854; 6,453,242; 6,534,261; 6,599,692; 6,503,717; 6,689,558; 7,030,215; 6,794,136; 7,067,317; 7,262,054; 7,070,934; 7,361,635; 7,253,273, all incorporated herein by reference in their entireties.

An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; 6,242,568; 6,733,970; 7,029,847; 7,700,523; and 8,618,024. In addition, enhancement of binding specificity for zinc finger binding domains has been described, for example, in U.S. Pat. No. 6,794,136.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

Selection of target sites; ZFPs and methods for design and construction of fusion proteins (and polynucleotides encoding same) are known to those of skill in the art and described in detail in U.S. Pat. Nos. 6,140,081; 5,789,538; 6,453,242; 6,534,261; 5,925,523; 6,007,988; 6,013,453; 6,200,759; 6,733,970; 6,746,838; 6,866,997; 7,029,847; 7,241,573; 7,241,574; 7,700,523; 8,618,024 and WO 02/099084.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

The CRISPR (clustered regularly interspaced short palindromic repeats) locus, which encodes RNA components of the system, and the cas (CRISPR-associated) locus, which encodes proteins (Jansen et al., 2002. *Mol. Microbiol.* 43: 1565-1575; Makarova et al., 2002. *Nucleic Acids Res.* 30: 482-496; Makarova et al., 2006. *Biol. Direct* 1: 7; Haft et al., 2005. *PLoS Comput. Biol.* 1:e60) make up the gene sequences of the CRISPR/Cas nuclease system. CRISPR loci in microbial hosts contain a combination of CRISPR-associated (Cas) genes as well as non-coding RNA elements capable of programming the specificity of the CRISPR-mediated nucleic acid cleavage.

The Type II CRISPR is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via Wastson-Crick base-pairing between the spacer on the crRNA and the protospacer on the target DNA next to the protospacer adjacent motif (PAM), an additional requirement for target recognition Finally, Cas9 mediates cleavage of target DNA to create a double-stranded break within the protospacer. Activity of the CRISPR/Cas system comprises of three steps: (i) insertion of alien DNA sequences into the CRISPR array to prevent future attacks, in a process called 'adaptation', (ii) expression of the relevant proteins, as well as expression and processing of the array, followed by (iii) RNA-mediated interference with the alien nucleic acid. Thus, in the bacterial cell, several of the so-called 'Cas' proteins are involved with the natural function of the CRISPR/Cas system and serve roles in functions such as insertion of the alien DNA etc.

In certain embodiments, Cas protein may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof. Suitable derivatives of a Cas polypeptide or a fragment thereof include but are not limited to mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some case, the cell does not naturally produce Cas protein and is genetically engineered to produce a Cas protein.

Thus, the nuclease comprises a DNA-binding domain in that specifically binds to a target site in any gene into which it is desired to insert a donor (transgene).

B. Cleavage Domains

Any suitable cleavage domain can be operatively linked to a DNA-binding domain to form a nuclease. For example, ZFP DNA-binding domains have been fused to nuclease domains to create ZFNs—a functional entity that is able to recognize its intended nucleic acid target through its engineered (ZFP) DNA binding domain and cause the DNA to be cut near the ZFP binding site via the nuclease activity. See, e.g., Kim et al. (1996) *Proc Natl Acad Sci USA* 93(3):1156-1160. More recently, ZFNs have been used for genome modification in a variety of organisms. See, for example, U.S. Pat. Nos. 7,888,121 and 8,409,861; United States Patent Publications 20030232410; 20050208489; 20050026157; 20060063231; and International Publication WO 07/014275. Likewise, TALE DNA-binding domains have been fused to nuclease domains to create TALENs. See, e.g., U.S. Pat. No. 8,586,526.

As noted above, the cleavage domain may be heterologous to the DNA-binding domain, for example a zinc finger DNA-binding domain and a cleavage domain from a nuclease or a TALEN DNA-binding domain and a cleavage domain, or meganuclease DNA-binding domain and cleavage domain from a different nuclease.

In other embodiments, the nuclease comprises an engineered TALE DNA-binding domain and a nuclease domain (e.g., endonuclease and/or meganuclease domain), also referred to as TALENs. Methods and compositions for engineering these TALEN proteins for robust, site specific interaction with the target sequence of the user's choosing have been published (see U.S. Pat. No. 8,586,526). In some embodiments, the TALEN comprises an endonuclease (e.g., FokI) cleavage domain or cleavage half-domain. In other embodiments, the TALE-nuclease is a mega TAL. These mega TAL nucleases are fusion proteins comprising a TALE DNA binding domain and a meganuclease cleavage domain. The meganuclease cleavage domain is active as a monomer and does not require dimerization for activity. (See Boissel et al., (20134) *Nucl Acid Res:* 42(4):2591-2601). In addition, the nuclease domain may also exhibit DNA-binding functionality.

In still further embodiments, the nuclease comprises a compact TALEN (cTALEN). These are single chain fusion proteins linking a TALE DNA binding domain to a TevI nuclease domain. The fusion protein can act as either a nickase localized by the TALE region, or can create a double strand break, depending upon where the TALE DNA binding domain is located with respect to the meganuclease (e.g., TevI) nuclease domain (see Beurdeley et al (2013) *Nat Comm:* 1-8 DOI: 10.1038/ncomms2782). Any TALENs may be used in combination with additional TALENs (e.g., one or more TALENs (cTALENs or FokI-TALENs) with one or more mega-TALs).

Heterologous cleavage domains can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) *Nucleic Acids Res.* 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) *Nucleases*, Cold Spring Harbor Laboratory Press, 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer Bitinaite et al. (1998) *Proc. Natl. Acad. Sci. USA* 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a FokI cleavage half-domain, can be used to reconstitute a catalytically active cleavage domain. Alternatively, a single polypeptide molecule containing a zinc finger binding domain and two Fok I cleavage half-domains can also be used. Parameters for targeted cleavage and targeted sequence alteration using zinc finger-Fok I fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in International Publication WO 07/014275, incorporated herein in its entirety. Additional restriction enzymes also contain separable binding and cleavage domains, and these are contemplated by the present disclosure. See, for example, Roberts et al. (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example, in U.S. Pat. Nos. 7,888,121 and 8,409,861; U.S. Patent Publication Nos. 20090305346 and 20080131962, the disclosures of all of which are incorporated by reference in their entireties herein. Amino acid residues at positions 446, 447, 479, 483, 484, 486, 487, 490, 491, 496, 498, 499, 500, 531, 534, 537, and 538 of Fok I are all targets for influencing dimerization of the Fok I cleavage half-domains.

Exemplary engineered cleavage half-domains of Fok I that form obligate heterodimers include a pair in which a first cleavage half-domain includes mutations at amino acid residues at positions 490 and 538 of Fok I and a second cleavage half-domain includes mutations at amino acid residues 486 and 499, for example engineered cleavage half-domains in which positions 490 (E→K) and 538 (I→K) in one cleavage half-domain are mutated to produce an engineered cleavage half-domain designated "E490K: I538K" and by mutating positions 486 (Q→E) and 499 (I→L) in another cleavage half-domain to produce an engineered cleavage half-domain designated "Q486E:I499L". The engineered cleavage half-domains described herein are obligate heterodimer mutants in which aberrant cleavage is minimized or abolished. See, e.g., U.S. Patent Publication No. 2008/0131962, the disclosure of which is incorporated by reference in its entirety for all purposes. In certain embodiments, the engineered cleavage half-domain comprises mutations at positions 486, 499 and 496 (numbered relative to wild-type Fold), for instance mutations that replace the wild type Gln (Q) residue at position 486 with a Glu (E) residue, the wild type Iso (I) residue at position 499 with a Leu (L) residue and the wild-type Asn (N) residue at position 496 with an Asp (D) or Glu (E) residue (also referred to as a "ELD" and "ELE" domains, respectively). In other embodiments, the engineered cleavage half-domain comprises mutations at positions 490, 538 and 537 (numbered relative to wild-type FokI), for instance mutations that replace the wild type Glu (E) residue at position 490 with a Lys (K) residue, the wild type Iso (I) residue at position 538 with a Lys (K) residue, and the wild-type His (H) residue at position 537 with a Lys (K) residue or a Arg (R) residue (also referred to as "KKK" and "KKR" domains, respectively). In other embodiments, the engineered cleavage half-domain comprises mutations at positions 490 and 537 (numbered relative to wild-type Fold), for instance mutations that replace the wild type Glu (E) residue at position 490 with a Lys (K) residue and the wild-type His (H) residue at position 537 with a Lys (K) residue or a Arg (R) residue (also referred to as "KIK" and "KIR" domains, respectively). (See US Patent Publication No. 20110201055). In other embodiments, the engineered cleavage half domain comprises the "Sharkey" and/or "Sharkey" mutations (see Guo et al, (2010) *J. Mol. Biol.* 400(1):96-107).

Engineered cleavage half-domains described herein can be prepared using any suitable method, for example, by site-directed mutagenesis of wild-type cleavage half-domains (Fok I) as described in U.S. Pat. No. 7,888,121; 20080131962; and 20110201055.

Alternatively, nucleases may be assembled in vivo at the nucleic acid target site using so-called "split-enzyme" technology (see e.g. U.S. Patent Publication No. 20090068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

Nucleases can be screened for activity prior to use, for example in a yeast-based chromosomal system as described in WO 2009/042163 and 20090068164. Nuclease expression constructs can be readily designed using methods known in the art. See, e.g., U.S. Pat. Nos. 7,888,121 and 8,409,861; U.S. Patent Publications 20030232410; 20050208489; 20050026157; 20060063231; and 20070134796. Expression of the nuclease may be under the control of a constitutive promoter or an inducible promoter, for example the galactokinase promoter which is activated (de-repressed) in the presence of raffinose and/or galactose and repressed in presence of glucose.

The Cas9 related CRISPR/Cas system comprises two RNA non-coding components: tracrRNA and a pre-crRNA array containing nuclease guide sequences (spacers) interspaced by identical direct repeats (DRs). To use a CRISPR/Cas system to accomplish genome engineering, both functions of these RNAs must be present (see Cong et al, (2013) *Sciencexpress* 1/10.1126/science 1231143). In some embodiments, the tracrRNA and pre-crRNAs are supplied via separate expression constructs or as separate RNAs. In other embodiments, a chimeric RNA is constructed where an engineered mature crRNA (conferring target specificity) is fused to a tracrRNA (supplying interaction with the Cas9) to create a chimeric cr-RNA-tracrRNA hybrid (also termed a single guide RNA). (see Jinek ibid and Cong, ibid).

Target Sites

As described in detail above, DNA domains can be engineered to bind to any sequence of choice. An engineered DNA-binding domain can have a novel binding specificity, compared to a naturally-occurring DNA-binding domain. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties. Rational design of TAL-effector domains can also be performed. See, e.g., U.S. Pat. No. 8,586,526.

Exemplary selection methods applicable to DNA-binding domains, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in co-owned WO 02/077227.

Selection of target sites; nucleases and methods for design and construction of fusion proteins (and polynucleotides encoding same) are known to those of skill in the art and described in detail in U.S. Pat. Nos. 7,888,121 and 8,409,861 Nos., incorporated by reference in their entireties herein.

In addition, as disclosed in these and other references, DNA-binding domains (e.g., multi-fingered zinc finger proteins) may be linked together using any suitable linker sequences, including for example, linkers of 5 or more amino acids. See, e.g., U.S. Pat. Nos. 6,479,626; 6,903,185; and 7,153,949 for exemplary linker sequences 6 or more amino acids in length. The proteins described herein may include any combination of suitable linkers between the individual DNA-binding domains of the protein. See, also, U.S. Pat. No. 8,586,526.

As noted above, the DNA-binding domains of the nucleases may be targeted to any gene. In certain embodiments, the nuclease (DNA-binding domain component) is targeted to a "safe harbor" locus, which includes, by way of example only, the AAVS1 gene (see U.S. Pat. No. 8,110,379), the CCR5 gene (see U.S. Publication No. 20080159996), the Rosa locus (see WO 2010/065123) and/or the albumin locus (see, U.S. Publication Nos. 20130177983 and 20130177960.

Donors

The present disclosure relates to nuclease-mediated targeted integration of an exogenous sequence into the genome of a cell using DNA minicircle (DNA MC) vectors. DNA MCs are episomal DNA vectors that are produced as circular expression cassettes lacking most or all of the bacterial plasmid DNA backbone. Accordingly, DNA MCs are typically smaller in size than plasmid vectors. DNA MCs can be made using methods known in the art, for example from parental plasmids. See, e.g., Mayrhofer et al. (2008) *J Gene Med.* 10(11):1253-69. doi: 10.1002/jgm.1243. The DNA MCs as described herein may include some residual plasmid backbone sequences from the parent plasmid so long as the residual sequences are not of bacterial origin so that the DNA MC is devoid of bacterial sequences. For example, the MCs may retain an attR recombination site and/or a 'multiple cloning site' that facilitates construction of a specific MC. Typically, the DNA MCs as described herein comprise residual (non-bacterial) plasmid sequences of less than 300 base pairs, including, but not limited to, between 0 and 300 base pairs of residue plasmid backbone (or any number of base pairs therebetween), between 0 and 200 base pairs of residue plasmid backbone (or any number of base pairs therebetween), or between 0 and 100 base pairs of residue plasmid backbone (or any number of base pairs therebetween).

As noted above, insertion of an exogenous sequence (also called a "donor sequence" or "donor" or "transgene"), for example for correction of a mutant gene or for increased expression of a wild-type gene. It will be readily apparent that the donor sequence is typically not identical to the genomic sequence where it is placed. A donor sequence can contain a non-homologous sequence flanked by two regions of homology to allow for efficient HDR at the location of interest. Additionally, donor sequences can comprise a vector molecule containing sequences that are not homologous to the region of interest in cellular chromatin. A donor molecule can contain several, discontinuous regions of homology to cellular chromatin. For example, for targeted insertion of sequences not normally present in a region of interest, said sequences can be present in a donor nucleic acid molecule and flanked by regions of homology to sequence in the region of interest.

Described herein are methods of targeted insertion of any polynucleotides for insertion into a chosen location. Polynucleotides for insertion can also be referred to as "exogenous" polynucleotides, "donor" polynucleotides or molecules or "transgenes." The donor polynucleotide can be DNA or RNA, single-stranded and/or double-stranded and can be introduced into a cell in linear or circular form. See, e.g., U.S. Pat. No. 8,623,618 and U.S. Publication Nos. 20100047805 and 20110207221. The donor sequence(s) are preferably contained within a DNA MC, which may be introduced into the cell in circular or linear form. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) *Proc. Natl. Acad. Sci. USA* 84:4959-4963; Nehls et al. (1996) *Science* 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

A polynucleotide can be introduced into a cell as part of a vector molecule having additional sequences such as, for example, replication origins, promoters and genes encoding antibiotic resistance. Moreover, donor polynucleotides can be introduced as naked nucleic acid, as nucleic acid complexed with an agent such as a liposome or poloxamer, or can be delivered by viruses (e.g., adenovirus, AAV, herpesvirus, retrovirus, lentivirus and integrase defective lentivirus (IDLY)).

In certain embodiments, the double-stranded donor includes sequences (e.g., coding sequences, also referred to as transgenes) greater than 1 kb in length, for example between 2 and 200 kb, between 2 and 10 kb, between 0.5 and 2 kb or between 0.1 and 2 kb (or any value therebetween). The double-stranded donor also includes at least one nuclease target site, for example. In certain embodiments, the donor includes at least 2 target sites, for example for a pair of ZFNs or TALENs. Typically, the nuclease target sites are outside the transgene sequences, for example, 5' and/or 3' to the transgene sequences, for cleavage of the transgene. The nuclease cleavage site(s) may be for any nuclease(s). In certain embodiments, the nuclease target site(s) contained in the double-stranded donor are for the same nuclease(s) used to cleave the endogenous target into which the cleaved donor is integrated via homology-independent methods.

The donor is generally inserted so that its expression is driven by the endogenous promoter at the integration site, namely the promoter that drives expression of the endogenous gene into which the donor is inserted (e.g., globin, albumin, AAVS1, etc.). However, it will be apparent that the donor may comprise a promoter and/or enhancer, for example a constitutive promoter or an inducible or tissue specific promoter.

The donor molecule may be inserted into an endogenous gene such that all, some or none of the endogenous gene is expressed. In other embodiments, the transgene (e.g., with or without globin encoding sequences) is integrated into any endogenous locus, for example a safe-harbor locus. See, e.g., U.S. Pat. Nos. 8,110,379; 7,951,925 and U.S. Publication No. 20100218264.

Furthermore, although not required for expression, exogenous sequences may also include transcriptional or translational regulatory sequences, for example, promoters, enhancers, insulators, internal ribosome entry sites, sequences encoding 2A peptides and/or polyadenylation signals.

The transgenes carried on the donor sequences described herein may be isolated from plasmids, cells or other sources using standard techniques known in the art such as PCR. Donors for use can include varying types of topology, including circular supercoiled, circular relaxed, linear and the like. Alternatively, they may be chemically synthesized using standard oligonucleotide synthesis techniques. In addition, donors may be methylated or lack methylation. Donors may be in the form of bacterial or yeast artificial chromosomes (BACs or YACs).

The double-stranded donor polynucleotides described herein may include one or more non-natural bases and/or backbones. In particular, insertion of a donor molecule with methylated cytosines may be carried out using the methods described herein to achieve a state of transcriptional quiescence in a region of interest.

The exogenous (donor) polynucleotide may comprise any sequence of interest (exogenous sequence). Exemplary exogenous sequences include, but are not limited to any polypeptide coding sequence (e.g., cDNAs), promoter sequences, enhancer sequences, epitope tags; marker genes, cleavage enzyme recognition sites and various types of expression constructs. Marker genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence.

In a preferred embodiment, the exogenous sequence (transgene) comprises a polynucleotide encoding any polypeptide of which expression in the cell is desired, including, but not limited to antibodies, antigens, enzymes, receptors (cell surface or nuclear), hormones, lymphokines, cytokines, reporter polypeptides, growth factors, and functional fragments of any of the above. The coding sequences may be, for example, cDNAs.

For example, the exogenous sequence may comprise a sequence encoding a polypeptide that is lacking or non-functional in the subject having a genetic disease, including but not limited to any of the following genetic diseases: achondroplasia, achromatopsia, acid maltase deficiency, adenosine deaminase deficiency (OMIM No. 102700), adrenoleukodystrophy, aicardi syndrome, alpha-1 antitrypsin deficiency, alpha-thalassemia, androgen insensitivity syndrome, pert syndrome, arrhythmogenic right ventricular dysplasia, ataxia telangictasia, barth syndrome, beta-thalassemia, blue rubber bleb nevus syndrome, canavan disease, chronic granulomatous diseases (CGD), cri du chat syndrome, cystic fibrosis, dercum's disease, ectodermal dysplasia, fanconi anemia, fibrodysplasia ossificans progressive, fragile X syndrome, galactosemis, Gaucher's disease, generalized gangliosidoses (e.g., GM1), hemochromatosis, the hemoglobin C mutation in the 6$^{th}$ codon of beta-globin (HbC), hemophilia, Huntington's disease, Hurler Syndrome, hypophosphatasia, Klinefleter syndrome, Krabbes Disease, Langer-Giedion Syndrome, leukocyte adhesion deficiency (LAD, OMIM No. 116920), leukodystrophy, long QT syndrome, Marfan syndrome, Moebius syndrome, mucopolysaccharidosis (MPS), nail patella syndrome, nephrogenic diabetes insipdius, neurofibromatosis, Neimann-Pick disease, osteogenesis imperfecta, porphyria, Prader-Willi syndrome, progeria, Proteus syndrome, retinoblastoma, Rett syndrome, Rubinstein-Taybi syndrome, Sanfilippo syndrome, severe combined immunodeficiency (SCID), Shwachman syndrome, sickle cell disease (sickle cell anemia), Smith-Magenis syndrome, Stickler syndrome, Tay-Sachs disease, Thrombocytopenia Absent Radius (TAR) syndrome, Treacher Collins syndrome, trisomy, tuberous sclerosis, Turner's syndrome, urea cycle disorder, von Hippel-Landau disease, Waardenburg syndrome, Williams syndrome, Wilson's disease, Wiskott-Aldrich syndrome, X-linked lymphoproliferative syndrome (XLP, OMIM No. 308240).

Additional exemplary diseases that can be treated by targeted integration include acquired immunodeficiencies, lysosomal storage diseases (e.g., Gaucher's disease, GM1, Fabry disease and Tay-Sachs disease), mucopolysaccahidosis (e.g. Hunter's disease, Hurler's disease), hemoglobinopathies (e.g., sickle cell diseases, HbC, α-thalassemia, β-thalassemia) and hemophilias.

In certain embodiments, the exogenous sequences can comprise a marker gene (described above), allowing selection of cells that have undergone targeted integration, and a linked sequence encoding an additional functionality. Non-limiting examples of marker genes include GFP, drug selection marker(s) and the like.

Additional gene sequences that can be inserted may include, for example, wild-type genes to replace mutated sequences. For example, a wild-type Factor IX gene sequence may be inserted into the genome of a stem cell in which the endogenous copy of the gene is mutated. The wild-type copy may be inserted at the endogenous locus, or may alternatively be targeted to a safe harbor locus.

Construction of such expression cassettes, following the teachings of the present specification, utilizes methodologies well known in the art of molecular biology (see, for example, Ausubel or Maniatis). Before use of the expression cassette to generate a transgenic animal, the responsiveness of the expression cassette to the stress-inducer associated with selected control elements can be tested by introducing the expression cassette into a suitable cell line (e.g., primary cells, transformed cells, or immortalized cell lines).

Furthermore, although not required for expression, exogenous sequences may also include transcriptional or translational regulatory sequences, for example, promoters, enhancers, insulators, internal ribosome entry sites, sequences encoding 2A peptides and/or polyadenylation signals. Further, the control elements of the genes of interest can be operably linked to reporter genes to create chimeric genes (e.g., reporter expression cassettes).

Targeted insertion of non-coding nucleic acid sequence may also be achieved. Sequences encoding antisense RNAs, RNAi, shRNAs and micro RNAs (miRNAs) may also be used for targeted insertions.

In additional embodiments, the donor nucleic acid may comprise non-coding sequences that are specific target sites for additional nuclease designs. Subsequently, additional nucleases may be expressed in cells such that the original donor molecule is cleaved and modified by insertion of another donor molecule of interest. In this way, reiterative integrations of donor molecules may be generated allowing for trait stacking at a particular locus of interest or at a safe harbor locus.

Delivery

The nucleases, polynucleotides encoding these nucleases, donor polynucleotides and compositions comprising the proteins and/or polynucleotides described herein may be delivered in vivo or ex vivo by any suitable means into any cell type.

Suitable cells include eukaryotic (e.g., animal or plant) and prokaryotic cells and/or cell lines. Non-limiting examples of such cells or cell lines generated from such cells include COS, CHO (e.g., CHO-S, CHO-K1, CHO-DG44, CHO-DUXB11, CHO-DUKX, CHOK1SV), VERO, MDCK, WI38, V79, B14AF28-G3, BHK, HaK, NS0, SP2/0-Ag14, HeLa, HEK293 (e.g., HEK293-F, HEK293-H, HEK293-T), and perC6 cells as well as insect cells such as *Spodoptera fugiperda* (Sf), or fungal cells such as *Saccharomyces, Pichia* and *Schizosaccharomyces* as well as plant cells from monocotyledonous or dicotyledonous plants In certain embodiments, the cell line is a CHO, MDCK or HEK293 cell line. Suitable cells also include stem cells such as, by way of example, embryonic stem cells, induced pluripotent stem cells, hematopoietic stem cells, neuronal stem cells and mesenchymal stem cells.

Methods of delivering nucleases as described herein are described, for example, in U.S. Pat. Nos. 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

Nucleases and/or donor constructs as described herein may also be delivered using vectors containing sequences encoding one or more of the ZFN(s), TALEN(s) or CRIPSR/Cas sytems. Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 6,534,261; 6,607,882; 6,824,978; 6,933,113; 6,979,539; 7,013,219; and 7,163,824, incorporated by reference herein in their entireties. Furthermore, it will be apparent that any of these vectors may comprise one or more of the sequences needed for treatment. Thus, when one or more nucleases and a donor construct are introduced into the cell, the nucleases and/or donor polynucleotide may be carried on the same vector or on different vectors (DNA MC(s)). When multiple vectors are used, each vector may comprise a sequence encoding one or multiple nucleases and/or donor constructs.

Conventional viral and non-viral based gene transfer methods can be used to introduce nucleic acids encoding nucleases and donor constructs in cells (e.g., mammalian cells) and target tissues. Non-viral vector delivery systems include DNA or RNA plasmids, DNA MCs, naked nucleic acid, and nucleic acid complexed with a delivery vehicle such as a liposome or poloxamer. Viral vector delivery systems include DNA and RNA viruses, which have either episomal or integrated genomes after delivery to the cell. For a review of in vivo delivery of engineered DNA-binding proteins and fusion proteins comprising these binding proteins, see, e.g., Rebar (2004) *Expert Opinion Invest. Drugs* 13(7):829-839; Rossi et al. (2007) *Nature Biotech.* 25(12):1444-1454 as well as general gene delivery references such as Anderson, *Science* 256:808-813 (1992); Nabel & Felgner, *TIBTECH* 11:211-217 (1993); Mitani & Caskey, *TIBTECH* 11:162-166 (1993); Dillon, *TIBTECH* 11:167-175 (1993); Miller, *Nature* 357:455-460 (1992); Van Brunt, *Biotechnology* 6(10):1149-1154 (1988); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* Doerfler and Bohm (eds.) (1995); and Yu et al., *Gene Therapy* 1:13-26 (1994).

Methods of non-viral delivery of nucleic acids include electroporation, lipofection, microinjection, biolistics, virosomes, liposomes, immunoliposomes, polycation or lipid:nucleic acid conjugates, naked DNA, artificial virions, and agent-enhanced uptake of DNA. Sonoporation using, e.g., the Sonitron 2000 system (Rich-Mar) can also be used for delivery of nucleic acids.

Additional exemplary nucleic acid delivery systems include those provided by Amaxa Biosystems (Cologne, Germany), Maxcyte, Inc. (Rockville, Md.), BTX Molecular Delivery Systems (Holliston, Mass.) and Copernicus Therapeutics Inc, (see for example U.S. Pat. No. 6,008,336). Lipofection is described in e.g., U.S. Pat. Nos. 5,049,386; 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Feigner, WO 91/17424, WO 91/16024.

The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiarmid et al (2009) *Nature Biotechnology* 27(7):643).

The use of RNA or DNA viral based systems for the delivery of nucleic acids encoding engineered ZFPs, TALEs and/or CRISPR/Cas systems take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of ZFPs include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher et al., *J. Virol.* 66:2731-2739 (1992); Johann et al., *J. Virol.* 66:1635-1640 (1992); Sommerfelt et al., *Virol.* 176:58-59 (1990); Wilson et al., *J. Virol.* 63:2374-2378 (1989); Miller et al., *J. Virol.* 65:2220-2224 (1991); PCT/US94/05700).

In applications in which transient expression is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38-47 (1987); U.S. Pat. No. 4,797,368; WO 93/24641; Kotin, *Human Gene Therapy* 5:793-801 (1994); Muzyczka, *J. Clin. Invest.* 94:1351 (1994). Construction of recombinant AAV vectors are described in a number of publications, including U.S. Pat. No. 5,173,414; Tratschin et al., *Mol. Cell. Biol.* 5:3251-3260 (1985); Tratschin, et al., *Mol. Cell. Biol.* 4:2072-2081 (1984); Hermonat & Muzyczka, *PNAS* 81:6466-6470 (1984); and Samulski et al., *J. Virol.* 63:03822-3828 (1989).

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al., *Blood* 85:3048-305 (1995); Kohn et al., *Nat. Med.* 1:1017-102 (1995); Malech et al., *PNAS* 94:22 12133-12138 (1997)). PA317/pLASN was the first therapeutic vector used in a gene therapy trial. (Blaese et al., *Science* 270:475-480 (1995)). Transduction efficiencies of 50% or greater have been observed for MFG-S packaged vectors. (Ellem et al., *Immunol Immunother.* 44(1):10-20 (1997); Dranoff et al., *Hum. Gene Ther.* 1:111-2 (1997).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al., *Lancet* 351:9117 1702-3 (1998), Kearns et al., *Gene Ther.* 9:748-55 (1996)). Other AAV serotypes, including AAV1, AAV2, AAV3, AAV4, AAV5, AAV6, AAV7, AAV8, AAV9 and AAVrh.10 and any novel AAV serotype can also be used in accordance with the present invention.

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector, is propagated in human 293 cells that supply deleted gene function in trans. Ad vectors can transduce multiple types of tissues in vivo, including nondividing, differentiated cells such as those found in liver, kidney and muscle. Conventional Ad vectors have a large carrying capacity. An example of the use of an Ad vector in a clinical trial involved polynucleotide therapy for antitumor immunization with intramuscular injection (Sterman et al., *Hum. Gene Ther.* 7:1083-9 (1998)). Additional examples of the use of adenovirus vectors for gene transfer in clinical trials include Rosenecker et al., *Infection* 24:1 5-10 (1996); Sterman et al., *Hum. Gene Ther.* 9:7 1083-1089 (1998); Welsh et al., *Hum. Gene Ther.* 2:205-18 (1995); Alvarez et al., *Hum. Gene Ther.* 5:597-613 (1997); Topf et al., *Gene Ther.* 5:507-513 (1998); Sterman et al., *Hum. Gene Ther.* 7:1083-1089 (1998).

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al., *Proc. Natl. Acad. Sci. USA* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Vectors (e.g., retroviruses, adenoviruses, liposomes, etc.) containing nucleases and/or donor constructs can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Vectors suitable for introduction of polynucleotides (e.g. nuclease-encoding and/or double-stranded donors) described herein include non-integrating lentivirus vectors (IDLV). See, for example, Ory et al. (1996) *Proc. Natl. Acad. Sci. USA* 93:11382-11388; Dull et al. (1998) *J. Virol.* 72:8463-8471; Zuffery et al. (1998) *J. Virol.* 72:9873-9880; Follenzi et al. (2000) *Nature Genetics* 25:217-222; U.S. Patent Publication No 20090117617.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., *Remington's Pharmaceutical Sciences,* 17th ed., 1989).

It will be apparent that the nuclease-encoding sequences and donor constructs can be delivered using the same or different systems. For example, the nucleases and donors can be carried by the same DNA MC. Alternatively, a donor polynucleotide can be carried by a MC, while the one or more nucleases can be carried by a standard plasmid or AAV vector. Furthermore, the different vectors can be administered by the same or different routes (intramuscular injection, tail vein injection, other intravenous injection, intraperitoneal administration and/or intramuscular injection. The vectors can be delivered simultaneously or in any sequential order.

Thus, the instant disclosure includes in vivo or ex vivo treatment of diseases and conditions that are amenable to insertion of a transgenes encoding a therapeutic protein, for example treatment of hemophilias via nuclease-mediated integration of clotting factors such as Factor VIII (F8). The compositions are administered to a human patient in an amount effective to obtain the desired concentration of the therapeutic polypeptide in the serum or the target organ or cells. Administration can be by any means in which the polynucleotides are delivered to the desired target cells. For example, both in vivo and ex vivo methods are contemplated. Intravenous injection to the portal vein is a preferred method of administration. Other in vivo administration modes include, for example, direct injection into the lobes of the liver or the biliary duct and intravenous injection distal to the liver, including through the hepatic artery, direct injection in to the liver parenchyma, injection via the hepatic artery, and/or retrograde injection through the biliary tree. Ex vivo modes of administration include transduction in vitro of resected hepatocytes or other cells of the liver, followed by infusion of the transduced, resected hepatocytes back into the portal vasculature, liver parenchyma or biliary tree of the human patient, see e.g., Grossman et al., (1994) *Nature Genetics,* 6:335-341.

The effective amount of nuclease(s) and donor to be administered will vary from patient to patient and according to the therapeutic polypeptide of interest. Accordingly, effective amounts are best determined by the physician administering the compositions and appropriate dosages can be determined readily by one of ordinary skill in the art. After allowing sufficient time for integration and expression (typically 4-15 days, for example), analysis of the serum or other tissue levels of the therapeutic polypeptide and comparison to the initial level prior to administration will determine whether the amount being administered is too low, within the right range or too high. Suitable regimes for initial and subsequent administrations are also variable, but are typified by an initial administration followed by subsequent administrations if necessary. Subsequent administrations may be administered at variable intervals, ranging from daily to annually to every several years. One of skill in the art will appreciate that appropriate immunosuppressive techniques may be recommended to avoid inhibition or blockage of transduction by immunosuppression of the delivery vectors, see e.g., Vilquin et al., (1995) *Human Gene Ther.,* 6:1391-1401.

Formulations for both ex vivo and in vivo administrations include suspensions in liquid or emulsified liquids. The active ingredients often are mixed with excipients which are pharmaceutically acceptable and compatible with the active ingredient. Suitable excipients include, for example, water, saline, dextrose, glycerol, ethanol or the like, and combinations thereof. In addition, the composition may contain minor amounts of auxiliary substances, such as, wetting or emulsifying agents, pH buffering agents, stabilizing agents or other reagents that enhance the effectiveness of the pharmaceutical composition.

As noted above, DNA constructs (e.g. DNA MCs) may be introduced into (e.g., into the genome of) a desired plant host by a variety of conventional techniques. For reviews of such techniques see, for example, Weissbach & Weissbach *Methods for Plant Molecular Biology* (1988, Academic Press, N.Y.) Section VIII, pp. 421-463; and Grierson & Corey, *Plant Molecular Biology* (1988, 2d Ed.), Blackie, London, Ch. 7-9. See, also, U.S. Pat. Nos. 8,399,218; 8,329,986; 8,329,986 and U.S. Publication No. and 20110189775, incorporated herein by reference in their entireties.

For example, the DNA construct may be introduced directly into the genomic DNA of the plant cell using techniques such as electroporation and microinjection of plant cell protoplasts, or the DNA constructs can be introduced directly to plant tissue using biolistic methods, such as DNA particle bombardment (see, e.g., Klein et al. (1987) *Nature* 327:70-73). Alternatively, the DNA construct can be introduced into the plant cell via nanoparticle transformation (see, e.g., U.S. Patent Publication No. 20090104700, which is incorporated herein by reference in its entirety). Alternatively, the DNA constructs may be combined with suitable T-DNA border/flanking regions and introduced into a conventional *Agrobacterium tumefaciens* host vector. *Agrobacterium tumefaciens*-mediated transformation techniques, including disarming of oncogenes and the development and use of binary vectors, are well described in the scientific literature. See, for example Horsch et al. (1984) *Science* 233:496-498, and Fraley et al. (1983) *Proc. Nat'l. Acad. Sci. USA* 80:4803.

In addition, gene transfer may be achieved using non-*Agrobacterium* bacteria or viruses such as *Rhizobium* sp. NGR234, *Sinorhizoboium meliloti, Mesorhizobium loti,* potato virus X, cauliflower mosaic virus and cassava vein mosaic virus and/ortobacco mosaic virus, See, e.g., Chung et al. (2006) *Trends Plant Sci.* 11(1):1-4.

The virulence functions of the *Agrobacterium tumefaciens* host will direct the insertion of a T-strand containing the construct and adjacent marker into the plant cell DNA when the cell is infected by the bacteria using binary T-DNA vector (Bevan (1984) *Nuc. Acid Res.* 12:8711-8721) or the co-cultivation procedure (Horsch et al. (1985) *Science* 227: 1229-1231). Generally, the *Agrobacterium* transformation system is used to engineer dicotyledonous plants (Bevan et al. (1982) *Ann. Rev. Genet* 16:357-384; Rogers et al. (1986) *Methods Enzymol.* 118:627-641). The *Agrobacterium* transformation system may also be used to transform, as well as transfer, DNA to monocotyledonous plants and plant cells. See U.S. Pat. No. 5,591,616; Hernalsteen et al. (1984) *EMBO J* 3:3039-3041; Hooykass-Van Slogteren et al. (1984) *Nature* 311:763-764; Grimsley et al. (1987) *Nature* 325:1677-179; Boulton et al. (1989) *Plant Mol. Biol.* 12:31-40; and Gould et al. (1991) *Plant Physiol.* 95:426-434.

Alternative gene transfer and transformation methods include, but are not limited to, protoplast transformation through calcium-, polyethylene glycol (PEG)- or electroporation-mediated uptake of naked DNA (see Paszkowski et al. (1984) *EMBO J* 3:2717-2722, Potrykus et al. (1985) *Molec. Gen. Genet.* 199:169-177; Fromm et al. (1985) *Proc. Nat. Acad. Sci. USA* 82:5824-5828; and Shimamoto (1989) *Nature* 338:274-276) and electroporation of plant tissues (D'Halluin et al. (1992) *Plant Cell* 4:1495-1505). Additional methods for plant cell transformation include microinjection, silicon carbide (e.g., WHISKERS™) mediated DNA uptake (Kaeppler et al. (1990) *Plant Cell Reporter* 9:415-418), and microprojectile bombardment (see Klein et al. (1988) *Proc. Nat. Acad. Sci. USA* 85:4305-4309; and Gordon-Kamm et al. (1990) *Plant Cell* 2:603-618).

Transformed plant cells which are produced by any of the above transformation techniques can be cultured to regenerate a whole plant which possesses the transformed genotype and thus the desired phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans, et al., "Protoplasts Isolation and Culture" in *Handbook of Plant Cell Culture*, pp. 124-176, Macmillian Publishing Company, New York, 1983; and Binding, *Regeneration of Plants, Plant Protoplasts*, pp. 21-73, CRC Press, Boca Raton, 1985. Regeneration can also be obtained from plant callus, explants, organs, pollens, embryos or parts thereof. Such regeneration techniques are described generally in Klee et al. (1987) *Ann. Rev. of Plant Phys.* 38:467-486.

Nucleic acids introduced into a plant cell can be used to confer desired traits on essentially any plant. A wide variety of plants and plant cell systems may be engineered for the desired physiological and agronomic characteristics described herein using the nucleic acid constructs of the present disclosure and the various transformation methods mentioned above. In preferred embodiments, target plants and plant cells for engineering include, but are not limited to, those monocotyledonous and dicotyledonous plants, such as crops including grain crops (e.g., wheat, maize, rice, millet, barley), fruit crops (e.g., tomato, apple, pear, strawberry, orange), forage crops (e.g., alfalfa), root vegetable crops (e.g., carrot, potato, sugar beets, yam), leafy vegetable crops (e.g., lettuce, spinach); flowering plants (e.g., petunia, rose, chrysanthemum), conifers and pine trees (e.g., pine fir, spruce); plants used in phytoremediation (e.g., heavy metal accumulating plants); oil crops (e.g., sunflower, rapeseed) and plants used for experimental purposes (e.g., *Arabidopsis*). Thus, the disclosed methods and compositions have use over a broad range of plants, including, but not limited to, species from the genera *Asparagus, Avena, Brassica, Citrus, Citrullus, Capsicum, Cucurbita, Daucus, Erigeron, Glycine, Gossypium, Hordeum, Lactuca, Lolium, Lycopersicon, Malus, Manihot, Nicotiana, Orychophragmus, Oryza, Persea, Phaseolus, Pisum, Pyrus, Prunus, Raphanus, Secale, Solanum, Sorghum, Triticum, Vitis, Vigna*, and *Zea*.

The introduction of nucleic acids into a plant cell can be used to confer desired traits on essentially any plant. In certain embodiments, the altered MDH expression/function in plant cells results in plants having increased amount of fruit yield, increased biomass of plant (or fruit of the plant), higher content of fruit flesh, concentrated fruit set, larger plants, increased fresh weight, increased dry weight, increased solids context, higher total weight at harvest, enhanced intensity and/or uniformity of color of the crop, altered chemical (e.g., oil, fatty acid, carbohydrate, protein) characteristics, etc.

One with skill in the art will recognize that an exogenous sequence can be transiently incorporated into a plant cell. The introduction of an exogenous polynucleotide sequence can utilize the cell machinery of the plant cell in which the sequence has been introduced. The expression of an exogenous polynucleotide sequence comprising a ZFN that is transiently incorporated into a plant cell can be assayed by analyzing the genomic DNA of the target sequence to identify and determine any indels, inversions, or insertions. These types of rearrangements result from the cleavage of the target site within the genomic DNA sequence, and the subsequent DNA repair. In addition, the expression of an exogenous polynucleotide sequence can be assayed using methods which allow for the testing of marker gene expression known to those of ordinary skill in the art. Transient expression of marker genes has been reported using a variety of plants, tissues, and DNA delivery systems. Transient analyses systems include but are not limited to direct gene delivery via electroporation or particle bombardment of tissues in any transient plant assay using any plant species of interest. Such transient systems would include but are not limited to electroporation of protoplasts from a variety of tissue sources or particle bombardment of specific tissues of interest. The present disclosure encompasses the use of any transient expression system to evaluate a site specific endonuclease (e.g., ZFN) and to introduce mutations within an MDH target gene. Examples of plant tissues envisioned to test in transients via an appropriate delivery system would include but are not limited to leaf base tissues, callus, cotyledons, roots, endosperm, embryos, floral tissue, pollen, and epidermal tissue.

One of skill in the art will recognize that an exogenous polynucleotide sequence can be stably incorporated in transgenic plants. Once the exogenous polynucleotide sequence is confirmed to be operable, it can be introduced into other plants by sexual crossing. Any of a number of standard breeding techniques can be used, depending upon the species to be crossed.

A transformed plant cell, callus, tissue or plant may be identified and isolated by selecting or screening the engineered plant material for traits encoded by the marker genes present on the transforming DNA. For instance, selection can be performed by growing the engineered plant material on media containing an inhibitory amount of the antibiotic or herbicide to which the transforming gene construct confers resistance. Further, transformed plants and plant cells can also be identified by screening for the activities of any visible marker genes (e.g., the β-glucuronidase, luciferase, B or C1 genes) that may be present on the recombinant nucleic acid constructs. Such selection and screening methodologies are well known to those skilled in the art.

Physical and biochemical methods also may be used to identify plant or plant cell transformants containing stably inserted gene constructs, or plant cell containing target gene altered genomic DNA which results from the transient expression of a site-specific endonuclease (e.g., ZFN). These methods include but are not limited to: 1) Southern blot analysis or PCR amplification for detecting and determining the structure of the recombinant DNA insert; 2) Northern blot, S1 RNase protection, primer-extension or reverse transcriptase-PCR amplification for detecting and examining RNA transcripts of the gene constructs; 3) enzymatic assays for detecting enzyme or ribozyme activity, where such gene products are encoded by the gene construct; 4) protein gel electrophoresis, Western blot techniques, immunoprecipitation, or enzyme-linked immunoassays (ELISA), where the gene construct products are proteins. Additional techniques, such as in situ hybridization, enzyme staining, and immunostaining, also may be used to detect the presence or expression of the recombinant construct in specific plant organs and tissues. The methods for doing all these assays are well known to those skilled in the art.

Effects of gene manipulation using the methods disclosed herein can be observed by, for example, Northern blots of the RNA (e.g., mRNA) isolated from the tissues of interest. Typically, if the mRNA is present or the amount of mRNA has increased, it can be assumed that the corresponding transgene is being expressed. Other methods of measuring gene and/or encoded polypeptide activity can be used. Different types of enzymatic assays can be used, depending on the substrate used and the method of detecting the increase or decrease of a reaction product or by-product. In addition, the levels of polypeptide expressed can be measured immunochemically, i.e., ELISA, RIA, EIA and other antibody based assays well known to those of skill in the art, such as by electrophoretic detection assays (either with staining or western blotting). As one non-limiting example, the detection of the AAD-1 and PAT proteins using an ELISA assay is described in U.S. Pat. No. 7,838,733, which reference is hereby incorporated by reference in its entirety herein. A transgene may be selectively expressed in some tissues of the plant or at some developmental stages, or the transgene may be expressed in substantially all plant tissues, substantially along its entire life cycle. However, any combinatorial expression mode is also applicable.

The present disclosure also encompasses seeds of the transgenic plants described above wherein the seed has the transgene or gene construct. The present disclosure further encompasses the progeny, clones, cell lines or cells of the transgenic plants described above wherein said progeny, clone, cell line or cell has the transgene or gene construct.

Fusion proteins (e.g., ZFNs) and expression vectors encoding fusion proteins can be administered directly to the plant for gene regulation, targeted cleavage, and/or recombination. In certain embodiments, the plant contains multiple paralogous MDH target genes. Thus, one or more different fusion proteins or expression vectors encoding fusion proteins may be administered to a plant in order to target one or more of these paralogous genes in the plant.

Administration of effective amounts is by any of the routes normally used for introducing fusion proteins into ultimate contact with the plant cell to be treated. The ZFPs are administered in any suitable manner, preferably with acceptable carriers. Suitable methods of administering such modulators are available and well known to those of skill in the art, and, although more than one route can be used to administer a particular composition, a particular route can often provide a more immediate and more effective reaction than another route.

Carriers may also be used and are determined in part by the particular composition being administered, as well as by the particular method used to administer the composition. Accordingly, there is a wide variety of suitable formulations of carriers that are available.

The following Examples relate to exemplary embodiments of the present disclosure in which the nuclease comprises a zinc finger nuclease (ZFN). It will be appreciated that this is for purposes of exemplification only and that other nucleases can be used, for instance TALENs, CRISPR/Cas systems, homing endonucleases (meganucleases) with engineered DNA-binding domains and/or fusions of naturally occurring of engineered homing endonucleases (meganucleases) DNA-binding domains and heterologous cleavage domains.

EXAMPLES

Example 1: Nucleofection of CD34+ HSC

To evaluate toxicity of DNA MC as compared to standard plasmids, experiments were carried out in human CD34+ HSC using donors encoding GFP. Briefly, fresh fetal liver HSC were isolated using standard methods that involve obtaining single cell suspensions of the tissue and then isolating the CD34+ fraction that contained the HSC using magnetic bead technology (Miltenyi Biotech). Nucleofection of the HSC was carried out using an Amaxa 4D nucleofector using the CD34 program. mRNAs encoding CCR5-specific ZFNs were made using the standard methods such as the mMessage mMachine T7 transcription kit, and by using the manufacturer's protocols (Ambion) and then nucleofected into the cells along with either the plasmid donor or the MC DNA.

For the plasmid donor samples, 3.75 µg of each CCR5 ZFN mRNA were used together with 5 µg of the plasmid DNA donor, while for the DNA MC samples, 3.75 µg of each CCR5 ZFN mRNA were used together with 0.5 µg of the MC donor. The different DNA donor amounts used were based on optimized amounts for each type of donor and the lower amounts of the MC DNA were possible because of its greater activity as a donor sequence. CCR5 ZFNs are described in U.S. Pat. Nos. 7,951,925 and 8,524,221), and maps of the plasmid and DNA MC donors are illustrated in FIG. 1.

Following nucleofection, the cells were allowed to recover overnight at 30° C., and then were analyzed for viability by 7-AAD exclusion as described in *Current Protocols in Flow Cytometry*.

Figure 2:
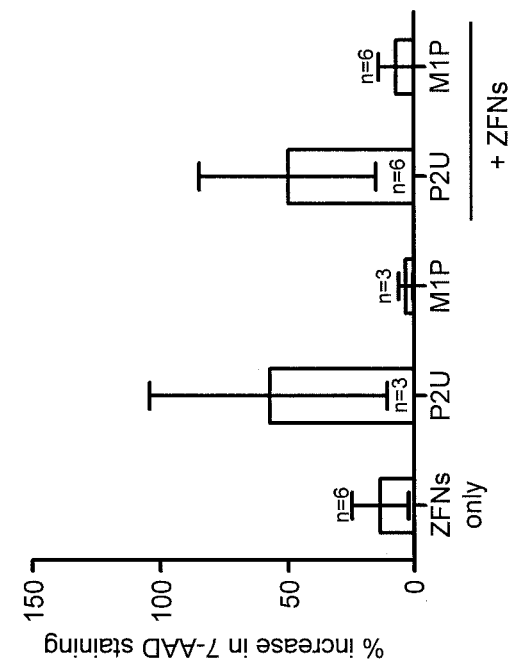
FIG. 2, panels A to C, depict the results regarding cell toxicity in human HSC following electroporation using the standard plasmid donors as compared to the MC donors. The ZFNs, when present, were expressed from in vitro transcribed mRNAs.
Figure 2:
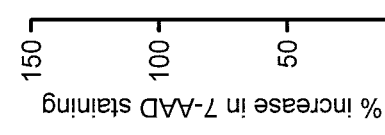

A comparison of the plasmid P2U with the DNA MC M1P showed that the minicircle was significantly less toxic to the cells as compared to the plasmid donor (see FIG. 2A). This same trend was found when the plasmid P2U was compared to DNA MC M2U or the PCR product PCR2U, both in the presence and absence of the ZFN (see FIG. 2B).

In addition, HSCs were nucleofected with ZFN mRNAs in combination with either plasmid P2U or minicircle M2U. The methods used, were as described in previous experiments. At 2 hours post-nucleofection, the levels of transcripts corresponding to IFNβ, ISG15, ISG54, ISG54 or CXCL10 were measured by quantitative Reverse-Transcriptase PCR, and the results plotted as the fold-increase in levels above the baseline recorded for untreated control HSC.

Figure 2C:
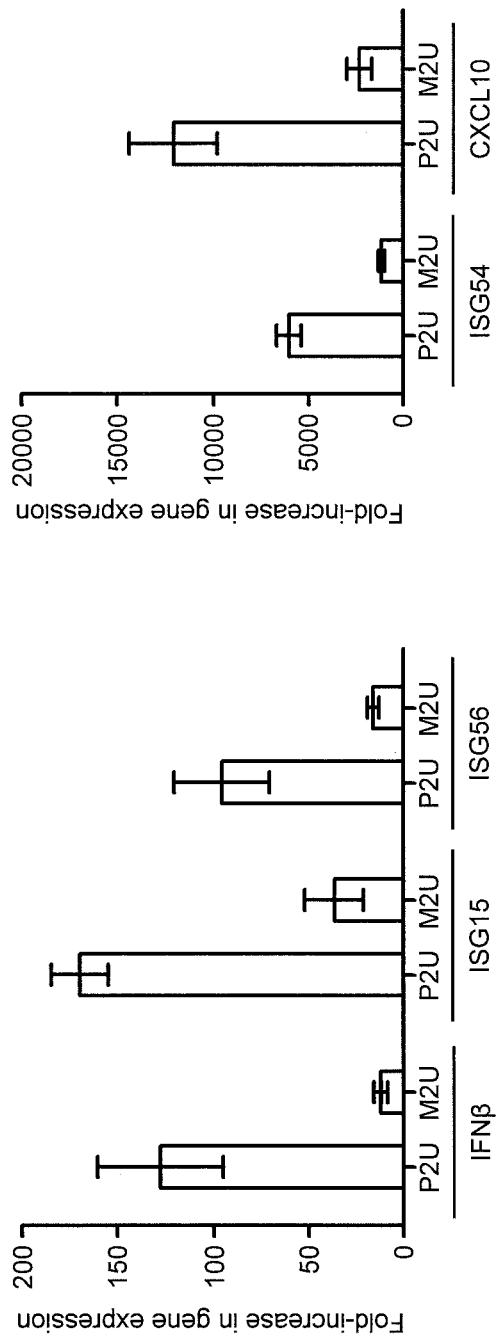
FIG. 2C depicts the fold-increase of expression of the indicated genes (IFNβ, ISG15, ISG56, ISG54 and CXCL10), 2 hours after the administration of plasmid donor P2U or the MC donor M2U. The rapid induction of expression of these genes results from the sensing of the introduced nucleic acid as foreign, and leads to cytotoxicity.

As shown in FIG. 2C, the plasmid DNA highly induces interferon-stimulated genes (ISGs) and IFNβ, which likely contributes to the overall toxicity caused by the plasmid DNA. In contrast, the minicircle DNA donor M2U induced significantly less expression of the ISGs.

Example 2: Engraftment of Engineered CD34+ HSC into NSG Mice

Human CD34+ HSC that had been nucleofected with the various plasmid and minicircle donor constructs as described above were used to engraft NSG mice to make "humanized mice" using standard protocols, for example as described in Holt et al. 2010, *Nature Biotech.* 28:839-47. Samples were taken from the peripheral blood of the mice by standard methodology at 4, 8, 12, 16, and 20 weeks post engraftment, also as described in Holt et al. 2010, *Nature Biotech.* 28:839-47.

Figure 3:
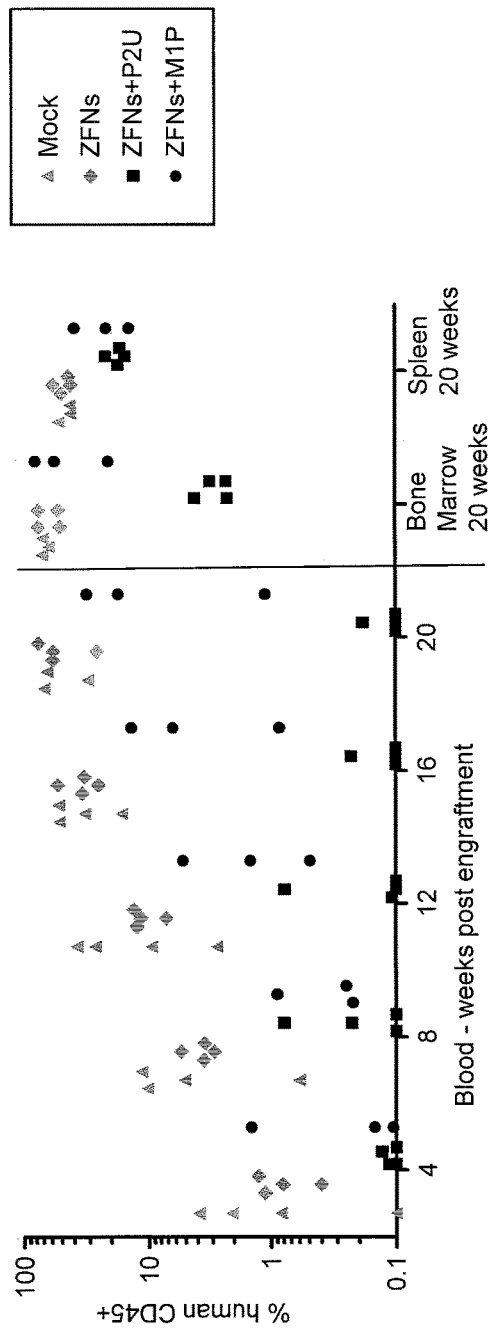
FIG. 3, panels A to D, depict the effect of plasmid and MC donors on the subsequent engraftment and differentiation of human HSC into CD45+ leucocytes in vivo.
Figure 3:
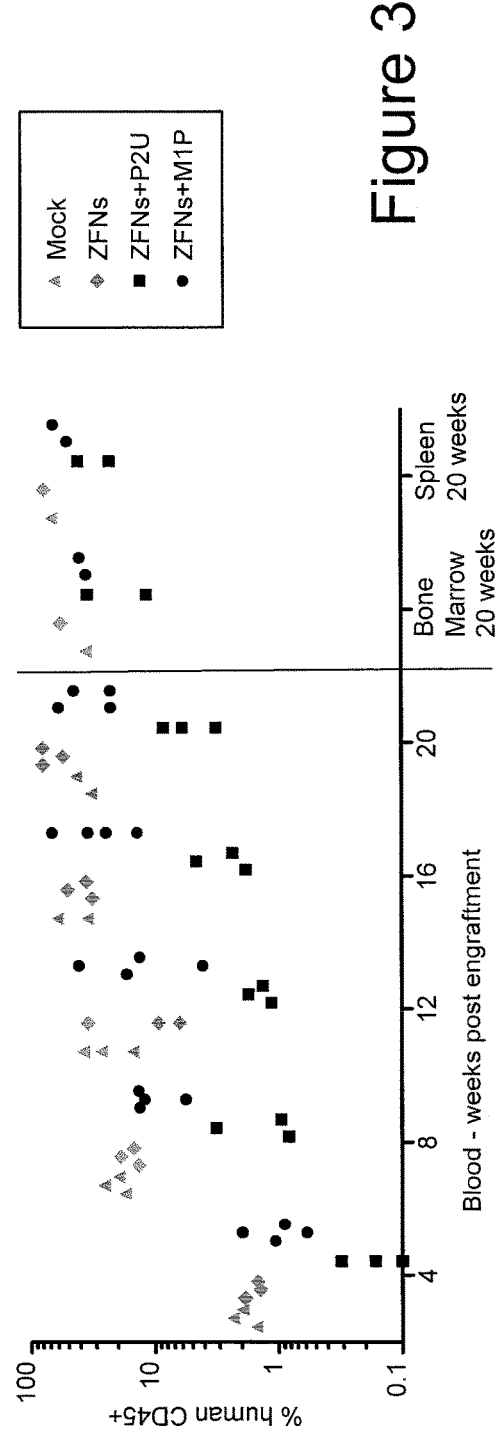
Figure 3:
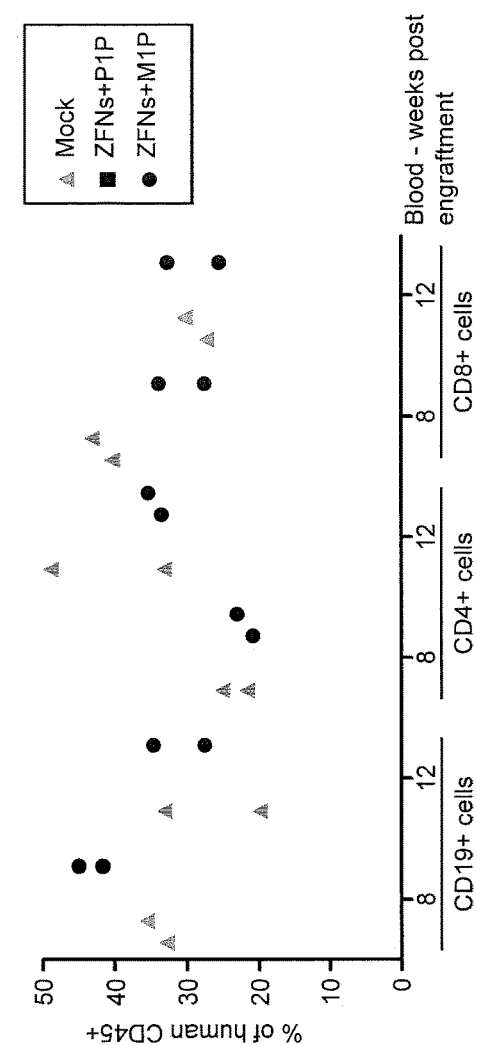
Figure 3:
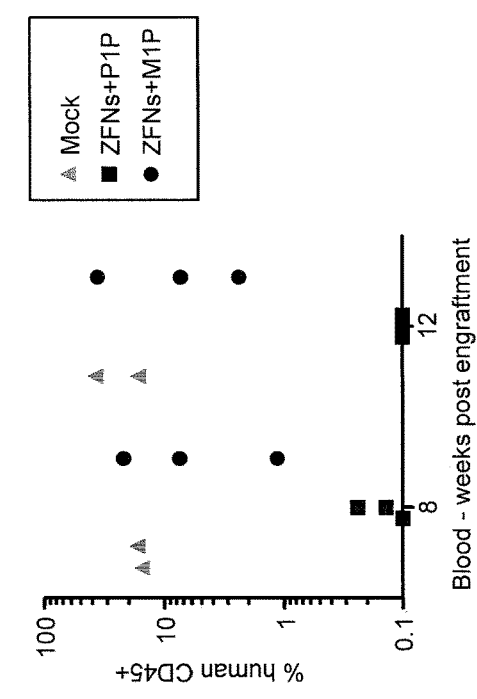

The ability of the human HSC to successfully engraft the mice and subsequently give rise to human CD45+ progeny blood cells was analyzed by evaluating the expression of human CD45 on leucocytes by FACs analysis, also described in Holt et al. (2010) *Nature Biotech.* 28:839-47. The experiments showed that cells that had been transformed with the DNA MCs showed improved viability and engrafted to a greater extent than those populations that had been treated with the plasmid donor (see FIG. 3A). Additionally, at 20 weeks, the animals were sacrificed and an analysis was done to determine the percent of human CD45 positive cells in the blood, bone marrow and spleen by FACs analysis as described above.

The results showed that the cells that had been nucleofected with the DNA MC were able to establish themselves in the NSG mouse tissues such as bone marrow and spleen to a higher extent than the human HSC that received the plasmid DNA donor. See, FIG. 3A.

The experiments were repeated with a second cohort of NSG mice, and the results were similar. See, FIG. 3B.

Additionally, an experiment was performed comparing nucleofection of human HSC with ZFNs and either P1P or M1P, but in this experiment, the human HSC were injected into neonatal NSG mice, which allowed a better analysis of the ability of the HSC to subsequently differentiate and produce the different lineages of human blood cells such as Cd19+ B cells and CD4+ and CD8+ T cells. Blood samples were analyzed at 8 and 12 weeks for the presence of the total human CD45+ population as a measure of engraftment, and for any samples that had greater than 5% human CD45+ cells (FIG. 3C), it was also possible to further analyze the cells by FACS for markers of the different lineages (B cells, and CD4 and CD8 T cells). The results showed that cells treated with the MC DNA differentiated to produce these different subsets. See, FIG. 3D. In contrast, the very low level of engraftment of the cells treated with the P1P plasmid, (see, FIG. 3C), meant that no lineage analysis could be performed.

Example 3: Transgene Insertion

Figure 4:
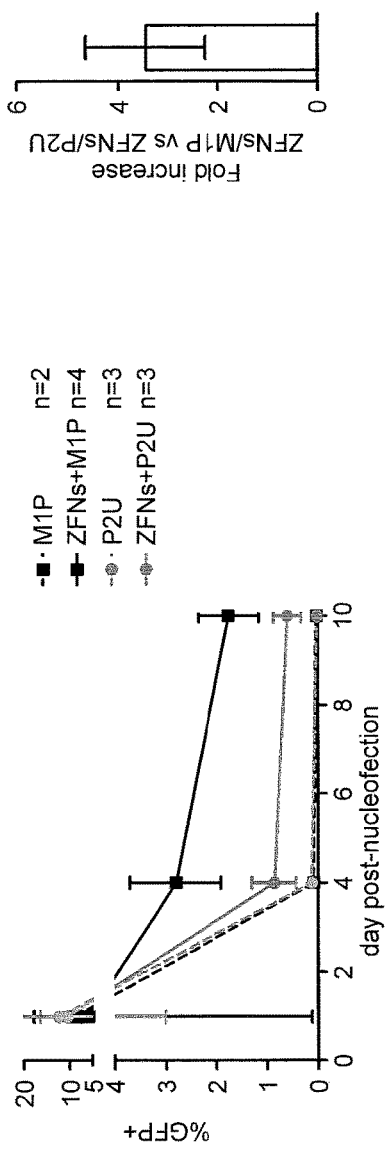
FIG. 4, panels A to C, are graphs depicting the rates of transgene integration through homologous recombination in HSC when the transgene is provided by M1P, P2U, P1P, M2U or PCR2U.
Figure 4:
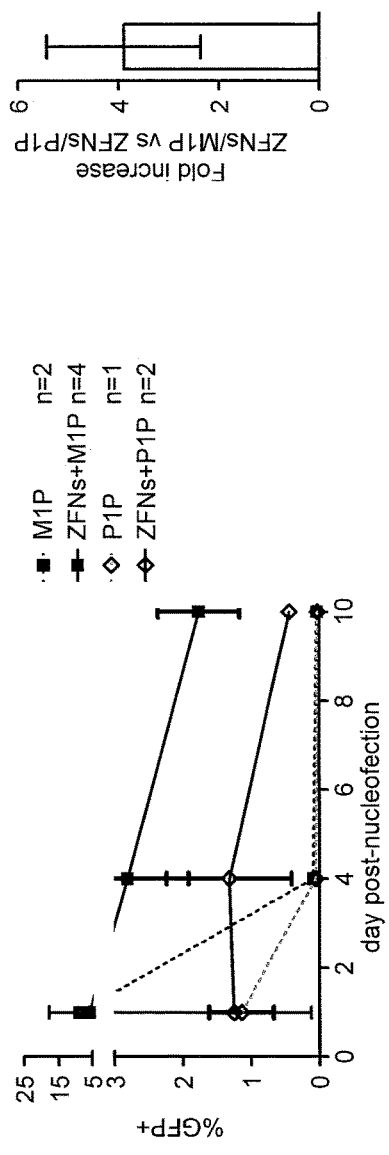
Figure 4C:
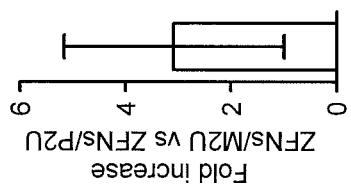
FIG. 4C depicts comparison of P2U with M2U and PCR2U. In all instances, the DNA MC donors gave better levels of targeted integration than the plasmid or PCR donors.
Figure 4C:
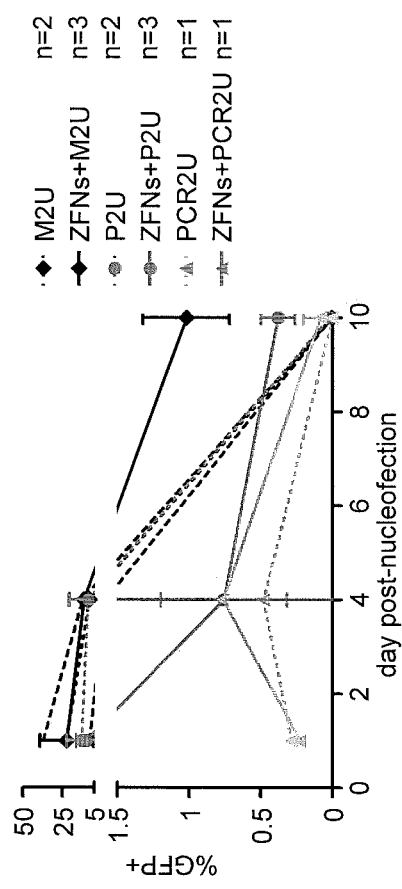

To confirm that the GFP transgene donor carried on the MC had integrated in the nucleofected human HSC, GFP expression was analyzed for up to ten days post nucleofection by FACs analysis to detect GFP+ cells, using standard protocols such as those described in *Current Protocols in Flow Cytometry*. By 4-10 days in culture, cells that did not receive the nucleases (ZFNs) had reverted to only background levels of GFP expression. By contrast, co-transfection of the ZFNs with a donor allowed stable GFP expression at higher levels due to integration of the GFP transgene. In all cases (see FIG. 4), cells that had been transfected with the GFP transgene on a DNA MC were the highest expressers of the GFP transgene.

Figure 5:
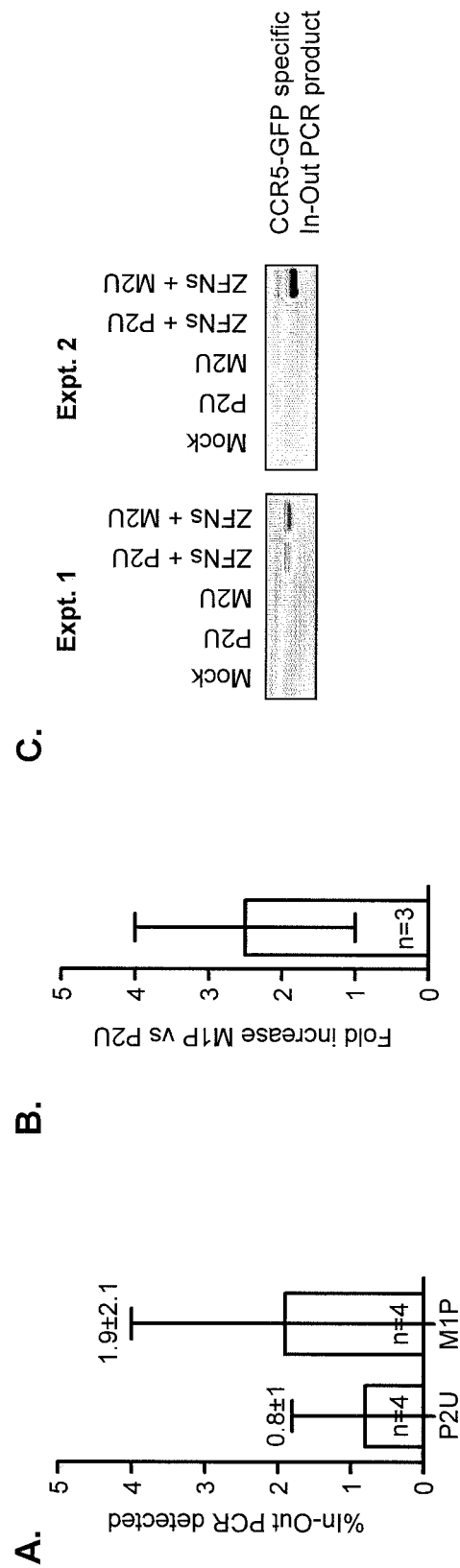
FIG. 5, panels A to C, depict the amount of targeted integration in the presence of ZFNs when donor is delivered via P2U, M1P, P2U or M2U, as assayed by an "in-out" PCR assay where targeted integration is measured by using one primer in the GFP transgene and one in the genome neighboring the ZFN target site, but beyond the extent of the homologous sequences contained in the donor. Consequently, a PCR product will only be generated if the transgene has integrated specifically at the locus targeted by the ZFNs.

Transgene integration at the specific target site (in these examples at the CCR5 locus) was also measured by "in/out PCR" using the primers 5'-GAG GAT TGG GAA GAC AAT AGC AG-3' (SEQ ID NO:1) and 5'-CCA GCA ATA GAT GAT CCA ACT CAA ATT CC-3' (SEQ ID NO:2) and methods previously described (Lombardo et al. *Nature Biotech.* 2007) and the results indicated that approximately 2.5 fold more plasmid integrated in samples receiving the DNA MCs than in samples receiving the donor plasmid (See FIG. 5). These results show that the MC configuration is less toxic and a superior donor template than either plasmid DNA or a linear PCR DNA product.

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. A method of expressing a transgene in an isolated human hematopoietic stem cell (HSC), the method comprising:
   a) administering at least one polynucleotide to an isolated human HSC, the polynucleotide encoding a pair of zinc finger nucleases (ZFNs) that generates a double-stranded break in the albumin, CCR5 or AAVS1 gene; and
   b) administering a non-viral DNA construct to the human HSC, the DNA construct comprising:
      (i) a nucleic acid comprising a transgene encoding a marker protein flanked by nucleic acid sequences homologous to the albumin, CCR5 or AAVS1 gene; and
      (ii) a plasmid backbone sequence that is less than 300 base pairs in length and is devoid of bacterial sequences,
   wherein the DNA construct does not include an origin of replication, and further wherein the nucleic acid encoding the transgene is integrated into the double-stranded break such that the marker protein is expressed in the isolated human HSC.

2. The method of claim 1, wherein the DNA construct comprises a promoter that drives expression of the marker protein.

* * * * *